United States Patent [19]

Schäfer et al.

[11] Patent Number: 4,699,133
[45] Date of Patent: Oct. 13, 1987

[54] PROCESS FOR PRODUCING A COHESIVE, SELF-ADHESIVE, RIGID OR ELASTIC BANDAGE FOR FIXING, COMPRESSION AND SUPPORT DRESSINGS FOR MEDICAL PURPOSES AND BANDAGE PRODUCED BY THIS PROCESS

[75] Inventors: Ewald Schäfer, Wolfstein; Harald Jung, Kreimbach-Kaulbach, both of Fed. Rep. of Germany

[73] Assignee: Firma Karl Otto Braun KG, Wolfstein, Fed. Rep. of Germany

[21] Appl. No.: 737,172

[22] Filed: May 23, 1985

Related U.S. Application Data

[63] Continuation-in-part of Ser. No. 715,034, Mar. 21, 1985, abandoned, which is a continuation of Ser. No. 594,542, Mar. 29, 1984, abandoned, which is a continuation of Ser. No. 131,429, Mar. 18, 1980, abandoned.

[30] Foreign Application Priority Data

Mar. 28, 1978 [DE] Fed. Rep. of Germany ....... 2912129

[51] Int. Cl.$^4$ .......................... A61L 15/00; B32B 3/10
[52] U.S. Cl. .................................. 128/156; 427/208.6; 428/196; 428/197; 428/230; 428/253; 428/257; 428/906
[58] Field of Search .................... 128/155, 156, 169; 427/2, 180, 208.6, 421; 428/196, 197, 230, 231, 240, 253, 254, 257, 317.3, 340, 341, 343, 906

[56] References Cited

U.S. PATENT DOCUMENTS

| 3,364,063 | 1/1968 | Satas | 128/156 |
| 3,523,528 | 8/1970 | Patience | 128/169 |
| 3,577,516 | 5/1971 | Gould et al. | 128/155 |
| 4,147,580 | 4/1979 | Buell | 128/287 |

FOREIGN PATENT DOCUMENTS 1491205 12/1974 Fed. Rep. of Germany.

Primary Examiner—William J. Van Balen
Attorney, Agent, or Firm—Toren, McGeady and Goldberg

[57] ABSTRACT

The invention relates to a cohesive, self-adhesive, rigid or elastic bandage for fixing, compression and support dressings and permanent elastic compression and support dressings for medical purposes and a process for the manufacture thereof. The bandage comprises a web of warp and weft threads or warp threads in the form of a woven fabric having a porous structure and an amount of ultra fine particles of an adhesive, such as a rubber adhesive, distributed over and bonded to both the exposed surfaces of the warp and weft threads to provide adhesive particles bonded to the threads on both sides of the fabric. The adhesive particles are uniformly distributed over both bandage surfaces without the fiber groups adhering to one another or to the projecting fiber ends of the two surfaces, the particles being of a size distribution and amount sufficient to provide adhesion between overlying bandage surfaces without substantially reducing the porosity and elasticity of the fabric.

13 Claims, 17 Drawing Figures

PROCESS FOR PRODUCING A COHESIVE, SELF-ADHESIVE, RIGID OR ELASTIC BANDAGE FOR FIXING, COMPRESSION AND SUPPORT DRESSINGS FOR MEDICAL PURPOSES AND BANDAGE PRODUCED BY THIS PROCESS

CROSS-REFERENCE TO RELATED APPLICATIONS

This is a continuation-in-part of copending application Ser. No. 715,034, filed Mar. 21, 1985, now abandoned, which, in turn, is a continuation of Ser. No. 594,542, filed Mar. 29, 1984, now abandoned, which, in turn, is a continuation of application Ser. No. 131,429, filed Mar. 18, 1980, now abandoned. The entire disclosures of these applications are incorporated herein by reference.

BACKGROUND OF THE INVENTION

1. Field of the Invention

The invention relates to a process for producing a cohesive, self-adhesive bandage, which does not adhere to the skin, hair and articles of clothing and which is rigid or elastic for fixing, compression and support dressings and permanent elastic compression and support dressings for medical purposes and a bandage produced by this process.

2. Description of the Prior Art

Dressing materials are known as compression and support dressings which, in order to obtain a self-adhering action, are coated on both sides with a contact adhesive in such a way that the adhesive, which is mainly formed from rubber, not only adheres to the outside of the warp and weft threads of the web, but also penetrates deeply into the porous fabric and fiber groups. Even the spaces or pores between the individual warp and weft threads are filled, so that it is no longer really a dressing material, but a rubber strip or band which contains an elastic reinforcing fabric to increase its tearing resistance in the warp and weft. In the case of such dressing materials, it is not possible to refer to individual adhesives particles because the rubber fills the entire volume of the pores, reducing or eliminating the porosity of the fabric, sealing the surface on either side like a film.

Due to the pronounced adhered state of the elastic warp threads in such bandages, the extensibility is greatly reduced, so that it is no longer possible to speak of a plastic behavior of such a bandage when applied to parts of the body with a very small radius. Furthermore, such bandages can only be stretched by about 30 to 40%. As a result of this construction, there is no breathing activity of the fibers, i.e., the bridge formation between skin and external air is lost. In addition, such an impregnation by an adhesive greatly influences the air permeability, water vapor permeability, and secretion absorptivity/water holding capacity, so that undesired heat and moisture chambers are formed which constitute an ideal medium for bacterial and fungal attacks to the skin. Furthermore, the extensibility is greatly reduced by the pronounced adhesion of the elastic elements, because the latter are very seriously negatively influenced in their elastic behavior due to the penetration of the adhesive into the fiber groups and through the covering or casing.

A reusable, elastic compression bandage for medical purposes is known and described in DE-AS No. 1,491,205. This bandage is in the form of an elongated support band made from an at least longitudinally extensible elastic material, the support band being partially coated on either side with a cohesive substance which adheres to itself but not to the skin or articles of clothing The cohesive substance is applied over the entire length of the support band onto those parts of the threads contained therewith which project from the fabric surface, while leaving substantially free the fabric gaps, so that the permeability for air and moisture is ensured. An elastic compression bandage constructed in this way is reusable and rests with a constant pressure on all sides on the body surface. Despite the elastic stress, there is no reduction in the pressure due to sliding of the individual turns of the bandage, particularly in the transverse direction, even when the part of the body carrying the bandage moves. This bandage is also intended to permit prolonged uninterrupted wear, i.e., it has good permeability for air and water vapor and, in particular, it does not adhere to the skin, hair or articles of clothing.

Whereas the adhesive coating can be applied to bandages by the dipping process, in the case of the bandage according to DE-AS No. 1,491,205, the adhesive coating is applied by rollers. In this process, rubber is removed from two spaced parallel tanks and transferred to two further rollers through which the bandage is then guided tangentially upwards. Following a fine adjustment, the two upper rollers uniformly apply the rubber to the bandage moved past. However, it is not possible to achieve such a fine adjustment which permits the coating in a uniform manner of both sides of the bandage. Depending on the density of the fabric, as a function of a more or less stretched state on being fed in, many portions of the bandage are not coated by the two rollers or are only coated on one side, so that portions, or even a complete side of the bandage remains without adhesive, whereas in certain areas of the bandage impregnation has taken place deep down into the said bandage. Therefore, the roller application process does not give a bandage having a uniform distribution of the rubber on both sides.

U.S. Pat. No. 3,364,063 to Satas describes a pressure-sensitive adhesive tape wherein the carrier material is a non-woven fabric and the adhesive substance is an adhesive polymer. The adhesive polymer is applied as a coating on the fibers of the non-woven fabric. Accordingly, the adhesive substance is an adhesive which adheres to skin and hair. FIG. 3 of this patent shows an almost completely closed adhesive, i.e., non-porous layer. This means that a self-adhesive tape has been provided, wherein the adhesive is applied, for example, by a spraying method. In order to obtain sufficient adhesiveness, it is necessary to place adhesive particles very densely on the surface, which has the result that the permeability to air and water is substantially reduced, i.e., the porosity of the fabric is reduced. In U.S. Pat. No. 3,364,063, a self-adhesive tape is produced which does not have any breathing activity of the fibers because the adhesive layer which is applied over the surface of the bandage material extends over the entire surface of the bandage material so that all threads of the fabric, i.e., the warp threads as well as the weft threads, firmly adhere to one another. The adhesive film closes the surface of the bandage fabric. In addition, the adhesive is applied under pressure to the surface of the bandage fabric so that there is no longer any air permeability of the bandage material. By applying the adhesive under pressure, the adhesive penetrates into the interior of the fiber groups and encloses the threads in such a way that the bandages produced are very negatively influenced in their elastic behavior.

U.S. Pat. No. 3,523,528 to Patience discloses spray-deposited discrete spots of, e.g., tacky rubbery material, latex, or resin on fabric substrates. The fabric is a woven, ribbon-like bandage having a low weight per surface area with ravel-resistant side edges, containing elastomeric warp yarns synthetic crimp stretch warp yarns and spun warp yarns (inelastic), wherein spun threads are wound or spun around, for example, the elastomeric warp yarns, so that a differentiated stretchability of the elastomeric warp yarns is achieved. In principle, these are bandages which for three decades have been used as compression bandages in different sequences between rigid and elastic warp threads. In order to obtain a differentiated stretchability of the entire bandage, it is necessary that the elastic threads always have material spun or wound around it, so that the elastomeric threads are limited in their elastic behavior.

When a bandage of this type is used, it loses its compressive power during wearing due to slackening. However, this is true in any elastic bandage because internal friction causes fatigue during wearing and the compression is thereby reduced. In other words, the energy, once expended, is not recovered in the form of compression, i.e., the efficiency must be lower than 100%. This fact is true in all bandage materials known to the experts and represents a "basic axiom of physics" because every material, even if it is razor blade steel, is subjected to fatigue when it is moved because of internal friction and plastic changes. The claims are also exclusively directed to the reduction of the compressive force during wearing of said bandages. This patent merely creates an elastic fabric which is provided with an adhesive layer, wherein this adhesive layer is applied on one side to the surface of the bandage material. It does not describe how the individual adhesive particles are applied to the surface of the bandage fabric or what type of elastic bandage is to be produced.

U.S. Pat. No. 3,577,516 to Gould, et al describes a "wound dressing" which is formed by spraying a hydrophilic, water insoluble polymer. This reference does not describe a porous textile fabric structure having a cohesive design, such as a self-adhesive bandage, but rather, a bandage which is prepared from a spray can. After being sprayed onto the surface of the skin, the polymer which is not water-soluble forms a film. This film is only permeable to air. The spray-on bandage is supposed to protect the wound from bacteria and from contamination from the air.

SUMMARY OF THE INVENTION

It is the object of the invention to provide a method for the production of a self-adhesive elastic bandage wherein the adhesive is applied in a uniform distribution on the surface of the bandage without causing the fiber packs to adhere to one another. It is a further object of this invention to provide a process of applying an adhesive to both sides of an elastic bandage in such a way that the fiber groups cannot adhere in themselves or to one another. It is still a further object of this invention to provide a cohesive, self-adhesive bandage which does not stick to the skin, hair and articles of clothing, which is either rigid or elastic and in which the adhesive, i.e., the rubber, is uniformly applied to both surfaces without the groups of fibers adhering to one another or to the projecting fiber ends of the two surfaces.

The foregoing objects as well as others are achieved by a cohesive, self-adhesive, rigid or elastic bandage for fixing, compression and support dressings and permanent elastic compression and support dressings for medical purposes and a process for the manufacture thereof. The bandage comprises a web of warp and weft threads or warp threads in the form of a woven fabric having a porous structure and an amount of ultra fine particles of an adhesive, such as a rubber adhesive, distributed over and bonded to both the exposed surfaces of the warp and weft threads to provide adhesive particles bonded to the threads on both sides of the fabric. The adhesive particles are uniformly distributed over both bandage surfaces without the fiber groups adhering to one another or to the projecting fiber ends of the two surfaces, the particles being of a size distribution and amount sufficient to provide adhesion between overlying bandage surfaces without substantially reducing the porosity and elasticity of the fabric.

DESCRIPTION OF THE PREFERRED EMBODIMENTS

Figure 1:
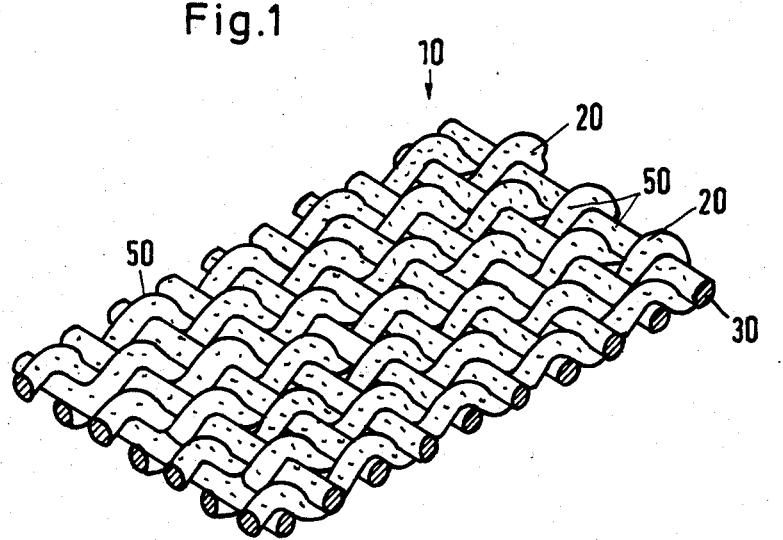
FIG. 1 is an enlarged perspective view of a portion of the fabric of the bandage of this invention covered by adhesive particles.

According to the present invention, an adhesive, such as, rubber or the like, is uniformly applied in the form of very fine particles and in a quantity of 1,000 to 5,000 particles per approximately 500 m$^2$ to the two surfaces of a flat bandage, which is in the form of a knitted fabric constituted by warp and weft, or warp only, while preventing the group of fibers from adhering to one another, whereby an adhesive is only applied to the projecting fiber ends in an application quantity of approximately 10 to 40 g/m$^2$ by the aerosol method, preferably by nozzle spraying in an eddy current.

The invention is also directed to a cohesive, self-adhesive rigid or elastic bandage which does not adhere to the skin, hair and articles of clothing in that the bandage comprises a web of warp and weft threads or warp threads only as a knitted or woven fabric with ultra fine particles of an adhesive, such as, rubber or the like, on either side of the exposed surface portions of the warp and weft threads in a distribution of 1000 to 5000 particles to approximately 500 mm$^2$, in an application quantity of approximately 10 to 40 g/m$^2$, whereby for most bandages a quantity of 15 to 20 g/m$^2$ is adequate.

The invention is also directed to an arrangement of 1000 to 5000 ultra fine particles of an adhesive, such as, rubber or the like, applied by an aerosol method preferably under an eddy current, to approximately 500 mm$^2$, in the case of an application quantity of approximately 10 to 40 g/m$^2$, to either side of the surface of a web of warp and threads or warp threads as a knitted fabric for the purpose of forming a cohesive, self-adhesive, rigid or elastic bandage which does not adhere to the skin, hair, articles of clothing for use for fixing, compression and support dressings and permanent elastic compression and support dressings for medical purposes.

With the process of the present invention, a rigid or elastic bandage is obtained in which the two sides are so finely and uniformly covered with rubber particles that a high cohesiveness holds together the individual turns and prevents sliding without there being any limitation to the macrophysical behavior, and consequently, the indication range, as compared with the non-cohesive bandage, i.e., despite the excellent adhesive characteristics, the different turns on the bandage only adhere to themselves and not to the skin, hair and articles of clothing. Additionally, the water vapor permeability, air permeability, secretion absorptivity and elastic behavior are in no way reduced in comparison with the non-cohesive bandage, so that heat localization and moisture chambers which are feared by doctors as the prerequisite for inflammation foci between the skin and bandage, cannot be formed. As a result of this cohesive construction of a bandage according to the process of the invention, the individual turns of the bandage are held in a slip-proof manner until the bandage is removed. Adhesiveness between the groups of fibers is prevented, particularly when using a minimum rubber application quantity and specifically approximately 10 to 40 g/m$^2$, approximately 15 to 20 g/m$^2$, based on the solid substance being adequate for most bandages, and as a result of the fact that the individual particles are very fine and are uniformly distributed on both sides of the bandage surface, so that maximum cohesiveness is obtained between the individual bandage turns, no matter how they are arranged.

With the extremely uniform distribution of the small particles, a genuine interlinking is ensured in all cases without there being any significant deterioration in the breathing activity. The small rubber particles applied to the bandage surfaces do not form a cohesive smeary or greasy application extending deep into the bandage, so that the individual particles cannot influence the physical behavior of the bandage, such as, for example, the extensibility, the reversible energy of deformation or the breathing activity. Furthermore, the elastic behavior of the bandage is in no way impaired.

Figure 2:
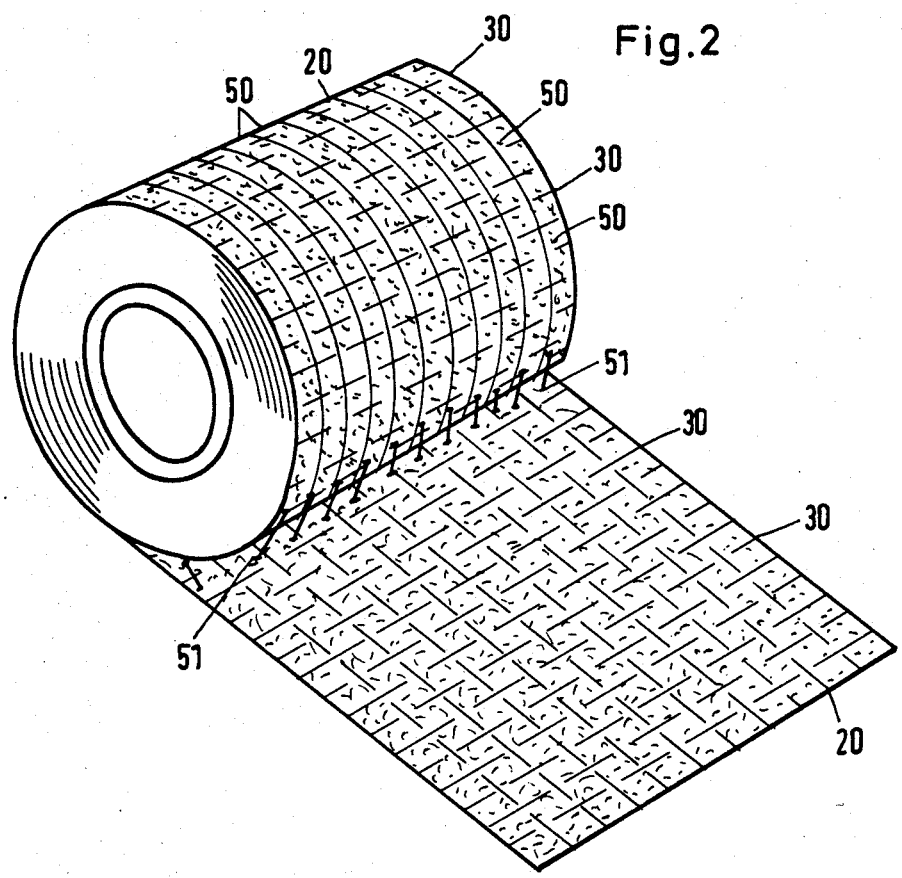
FIG. 2 is a perspective view of the bandage of this invention partly rolled up, the adhesive particles visible on the surface.
Figure 3:
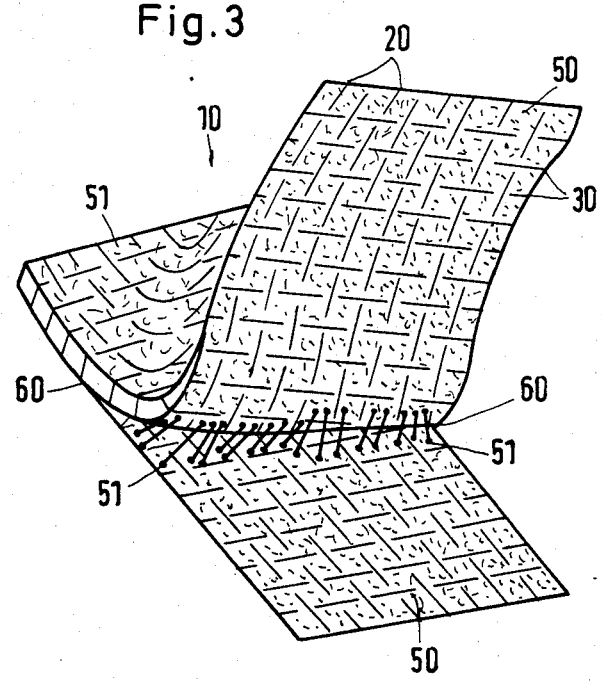
FIG. 3 is a perspective view of two fabric layers applied to one another, held together by the adhesive particles.
Figure 4:
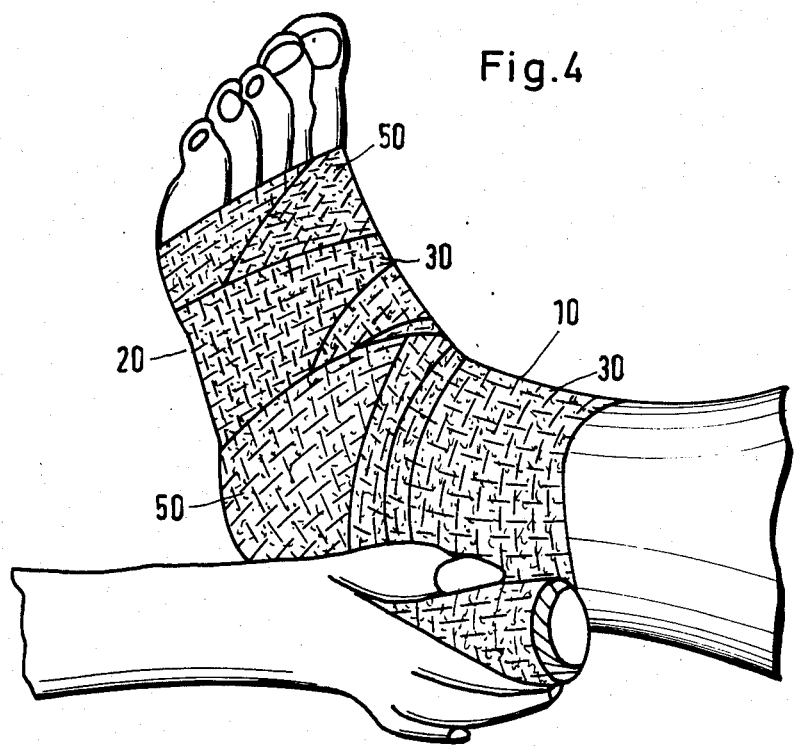
FIG. 4 is a perspective view of the bandage of this invention applied as a dressing.

The bandage produced according to the process of the invention is shown in the drawings, wherein FIG. 1 shows a fabric portion of the bandage in a larger scale plane view, the fabric surface being covered by rubber particles; FIG. 2 shows a bandage in a partly rolled up state, the rubber particles being clearly visible on the surface; FIG. 3 shows two fabric layers applied to one another held together at the separating line by rubber particles; FIG. 4 shows a dressing applied with a bandage according to the invention.

The bandage which is in the form of a web 10 has weft threads 20 and warp threads 30 (FIGS. 1 to 4). Very fine rubber particles 50 are applied by means of a known aerosol process to either side of the exposed surface portions of the warp and weft threads 20, 30. At 51 in FIGS. 2 and 3, it is possible to see pulled apart rubber particles between rolled up and already unrolled fabric portions. These ultra-fine particles 50 are applied in a distribution of 1,000 to 5,000 particles to approximately 500 mm$^2$, the applied quantity being in a magnitude of 10 to 40g/m$^2$. FIGS. 2 and 3 in particular show the high adhesiveness of two bandage layers. FIG. 3 shows two fabric layers applied to one another and which are held together at separating lines 60 by rubber particles 51.

As to the term "woven fabric", it is clear by virtue of the fact that throughout the specification and claims, reference is made to a warp and weft, that it is a woven fabric which is being referred to. It is well known in the textile art that these two terms apply solely to a woven fabric.

The preferred value ranges of 15 to 20 g/m$^2$, 1,000 to 5,000 particles per 500 mm$^2$, and 10 to 40 g/m$^2$, are well understood by one skilled in the art. In the first instance, the amount of 1,000 to 5,000 particles per 500 mm$^2$ clearly relates to the distribution of the particles in terms of number of particles per area of the bandage. The weight relationship further defines the total amount of adhesive applied. The weight of the adhesive applied is influenced by the size of the particles which inherently could change the distribution. It is important that the size of the particles be such that an application of 1,000 to 5,000 particles per 500 mm$^2$ would produce an appropriate weight range of 10 to 40 g/m$^2$. These numerical values and parameters are clearly understandable by one skilled in the art.

The type adhesive particles used may be determined by one skilled in the art of self-adhesive bandages and dressing materials. Such adhesives are based either on mixtures of rubber, resins (which make the material sticky), and softeners, or on special polymers without other additions. The development of the adhesive bandage began with the American "rubber bandage" which uses a pressure-sensitive, self-adhesive substance. The disadvantages of such a bandage are the lack of adhesive power on the skin and the limited resistance to aging. Such limitations were corrected by adding zinc oxide. Such bandages were known as "LEUKOPLAST" bandages. The adhesive bandages currently used can be divided into two groups which differ in the type of self-adhesive substance used. This categorization also applies to self-adhesive dressing materials. One group is based on conventional self-adhesive rubber substances and the other on synthetic polymer compounds and polyaddition compounds. The conventional substances are developments which are based on the old zinc oxide - rubber formulae. It was believed that the self-adhesive characteristics of a substance could be traced back to the presence of two disperse phases. It has been determined in more recent studies that this is not accurate, but that the viscosity of the adhesive is the most important factor. The prerequisite for self-adhesive characteristics is a viscosity which is sufficient to moisten the surface. For practical usefulness, however, a sufficient cohesiveness is also required. In the conventional self-adhesive substances, the correct viscosity is obtained by adding auxiliary products to the cohesive rubber, and in the synthetic self-adhesive substances which are based on homopolymers or copolymers, the correct combination of viscosity and cohesiveness is obtained by adjusting the average molar substance and the distribution of the molar substance in the total polymer. In rubber self-adhesive substances, resins, softeners and fillers are used as the required auxiliary products. The most important rubbers are the natural rubbers, cis-1,4-polyisoprene, styrenebutadiene polymer, polyisobutylene and butyl rubber.

Colophonium and its derivatives, in addition to the polyterpene resins of $\beta$-pinene, the hydrocarbon resins which are produced from olefins of oil cracking are also used as resins.

EXAMPLES

By means of the following examples, the superiority of a bandage produced according to the process of this invention is demonstrated as compared with an elastic compression bandage (type 103), an elastic fixing bandage (type 181), and a permanent elastic compression bandage (type 600), specifically when treated according to the known dipping process and production process of DE-AS No. 1,491,205.

It has surprisingly been found that the particle size, uniform distribution, percentages of different sizes, state of the contact adhesive applied, i.e., the microphysical behavior, are not without macrophysical consequences. These properties greatly influence the overall physical behavior, such as, adhesiveness, energy of adhesion, aging, secretion absorptivity, air permeability, water vapor permeability, water holding capacity, extensibility behavior, etc. More detailed reference will be made hereinafter to the macrophysical behavior and consequently to the indication value of bandages 103, 181, and 600 finished by the dipping process, the roller application process, and the process of the present invention.

A dressing material, such as, a rigid or elastic lint fixing bandage like type 181, a compression and support bandage like type 103, whose elasticity can be attributed to the twisted crepe threads with different twisting characteristics, or a permanent elastic compression and support bandage of type 600, whose permanent elasticity is essentially due to the covered polyurethane or rubber fibers and/or textured, polyfilic, synthetic yarn, following such a cohesive construction there must be no significant differences compared with the values of an untreated bandage, i.e., the values which are very important for the treatment or healing of a wound. Good aging resistance of the adhesive, very good secretion absorptivity, good water holding capacity and air permeability, i.e., there must be a good bridge between the skin and the external air, are necessary to prevent the formation of heat and moisture chambers between skin and bandage which are feared because they form the prerequisite for bacterial attacks and inflammation. The listed indication values are given numerically for bandages of types 103, 181 and 600. Account is taken of the macrophysical values, such as extensibility, latex percentage, water holding capacity, air permeability, adhesiveness without added aging, adhesiveness after one year, two years, three years, etc., up to seven years are taken into account.

As can be gathered from Table 1, bandage 103 has an extensibility of 95% in the raw state. As there is a zero latex percentage, the water holding capacity according to Bundesmann is relatively high and specifically 70%. The air permeability according to Frank is 7 seconds. This figure gives the time in seconds for forcing 10 liters of air through the fabric under identical physical conditions. As the latex percentage of bandage 103 is zero, the adhesiveness is also zero. The adhesiveness is calculated as follows: A cohesive bandage is folded to a length of 10 cm and is then rolled together at a temperature of 37° C. with a roller weighing 5kp, 45 rolling movements being performed in a minute. The two ends are then secured in a stress-strain machine and the rolled-together 10 cm are pulled apart and the energy of adhesion is determined from the stress-strain diagram. The average adhesiveness can be determined from the path and the energy.

TABLE 1

| | | | | | Technical-Physical Data | | | | | | | |
| | | | Water- | Air- | | Adhesiveness in cN | | | | | | |
| | Extensibility % | Latex % | holding capacity % | permeability 10l/sec. | Without aging | after 1 year | after 2 years | after 3 years | after 4 years | after 5 years | after 6 years | after 7 years |
| --- | --- | --- | --- | --- | --- | --- | --- | --- | --- | --- | --- | --- |
| Bandage 103 basic product | 95 | 0 | 70 | 7.0 | — | — | — | — | — | — | — | — |
| Bandage 103 application process | 85 | 15 | 56 | 8.6 | 471 | 519 | 471 | 477 | 397 | 296 | 314 | 287 |
| Bandage 103 according to DE-AS 1,491,205 | 70 | 16 | 63 | 12.8 | 337 | 202 | 176 | 147 | 293 | 222 | 251 | 261 |
| Bandage 103 dipping process | 50 | 79 | 28 | 14.3 | 182 | 226 | 295 | 155 | 61 | 69 | 71 | 47 |

A cohesive bandage is aged at 70° C. over one or more days according to the formula $$\frac{a-1}{2} = x$$

in which a is the number of aging days and x is the aging years. Thus, if a bandage is stored for five 24-hour days in a dryer at 70° C., the formula gives $5-1=4:2=2$, i.e., the normal storage time of the bandage is two years. A seven year aging takes place according to formula $15-1=14:2=7$, i.e., the bandage must be stored for 15 days at a temperature of 70° C. Following this storage period, the individual samples are folded up to 10 cm and rolled together 45 times for one minute with a 5kp roller at a temperature of 37° C. As described hereinbefore, the two ends are then secured in the stress-strain machine and pulled apart. The energy of adhesion is determined from the stress-strain diagram and the average adhesiveness is determined from the course.

In accordance with the cohesive construction of a type 103 bandage by the process of the invention, the technological performance leads to the extensibility being reduced from 95 to 85%. This extensibility is large enough in order to be able to apply plastic dressings even to parts of the body with a relatively small radius.

With a latex proportion of 15%, based on the finished article, the water holding capacity drops from 70 to 66%, while the air permeability, i.e., for forcing 10 liters of air through the fabric, rises from 7.0 to 8.6 seconds. The adhesiveness is 471 cN with aging, and after aging for 1 year is 519 cN, after 2 years 471 cN, after 3 years 477 cN, after 4 years 397 cN, after 5 years 296 cN, after 6 years 314 cN, and after 7 years 287 cN.

Thus, the contact adhesive does not become greasy and therefore does not adhere to the skin, hair or items of clothing. A type 103 bandage was used for checking the individual values for its cohesive construction according to the dipping process. Due to the technological performance of the dipping process, the extensibility is reduced to almost 50%, i.e., the bandage loses 45 percentage points. The latex proportion was calculated as 79%, which explains the limited water holding capacity of only 28% and the high resistance to air permeability. Thus, the water holding capacity is only 28% compared with 70% in the untreated article. Under identical physical conditions, 14.3 seconds are required for forcing 10 liters of air through the bandage. Although the latex proportion is 79%, the adhesiveness without aging is only 182 cN. After aging for 1 year, it is 226 cN, after 2 years 295 cN, after 3 years 155 cN, after 4 years 61 cN, after 5 years 69 cN, after 6 years 71 cN, and after 7 years 47 cN, i.e., there is a pronounced reduction in the adhesiveness due to aging. Furthermore, after only 1 year the bandage which no longer just adheres to itself, instead adheres easily to hair, skin and clothing.

With a cohesive construction of a type 103 bandage according to DE-AS No. 1,491,205, the extensibility drops from 95 to 70%. According to this process, an extensibility range is obtained which is just sufficient to be able to apply plastic dressings, but with such extensibility values it is critical if the parts of the body have only a relatively small radius. The latex proportion is 16%. The water holding capacity has dropped from 70 to 63%, while the air permeability has risen to 12.8 seconds, i.e., under identical physical conditions 12.8 seconds are required in order to force 10 liters of air through the fabric. The adhesiveness without aging was 337 cN, after aging for 1 year 202 cN, after 2 years 176 cN, after 3 years 147 cN, after 4 years 293 cN, after 5 years 222 cN, after 6 years 251 cN, and after 7 years 261 cN.

Thus, the type 103 bandage cohesively finished according to the process of the invention only had a 10% extensibility loss, although the latex proportion was only 15%. The water holding capacity differed only insignificantly from the basic article. There was an insignificant reduction in the air permeability from 8.6 seconds to 7.0 seconds compared with the basic article. The type 103 bandage with 79% rubber cohesively finished by the dipping process has relatively low adhesiveness, despite the high rubber percentage and after 2 years this has increased to an extraordinary level. The water holding capacity of 28% drops to a very low level and the air permeability rises to 14.3 seconds, which is twice as high as in the basic article, i.e., with such a bandage it is to be expected that the bridge formation between skin and external air is disturbed so that moisture and heat chambers can form. The same bandage cohesively finished according to DE-AS No. 1,491,205 had an extensibility loss of 25%, i.e., the extensibility dropped from 95 to 70%. Thus, the extensibility is at the lower limit for permitting the application of plastic dressings, particularly to parts of the body with a small radius. The latex proportion was 16%. The water holding capacity decreased only insignificantly from 70 to 63% compared with the basic article. However, the air permeability dropped from 7.0 to 12.8 seconds and is therefore much less advantageous than with a bandage cohesively finished according to the invention. The adhesiveness without aging was 337 cN, after 1 year 202 cN, after 2 years 176 cN, after 3 years 147 cN, after 4 years 293 cN, after 5 years 222 cN, after 6 years 251 cN, and after 7 years 261 cN. Since the adhesiveness levels were lower than with a bandage cohesively finished according to the present invention, despite identical latex percentages, it can be assumed that the individual adhesive strips did not engage directly on one another or that the sides were cohesively impregnated to a differing degree.

The conditions are similar in the case of type 181 bandages according to Table 2.

TABLE 2

| | Technical-Physical Data | | | | | | | | | | |
|---|---|---|---|---|---|---|---|---|---|---|---|
| | Extensibility % | Latex % | Water-holding Capacity % | Air-permeability 10 l/sec. | Adhesiveness in cN | | | | | | |
| | | | | | Without aging | after 1 year | after 2 years | after 3 years | after 4 years | after 5 years | after 6 years | after 7 years |
| Bandage 181 basic product | 235 | 0 | 152 | 3.3 | — | — | — | — | — | — | — | — |
| Bandage 181 application process | 120 | 19 | 140 | 3.4 | 419 | 462 | 390 | 356 | 413 | 279 | 283 | 317 |
| Bandage 181 according to DE-AS 1,491,205 | 90 | 21 | 118 | 3.9 | 277 | 431 | 411 | 235 | 159 | 262 | 214 | 139 |
| Bandage 181 dipping proces | 40 | 79 | 67 | 4.2 | 289 | 176 | 145 | 222 | 159 | 140 | 76 | 13 |

The extensibility of the type 181 bandage which was not cohesively finished is 235%, the water holding capacity 152% and the air permeability 3.3 seconds. The bandage produced according to the process of the invention contains 19% latex and has an extensibility loss of 115%, decreasing from 235 to 120%. The water holding capacity of the bandage decreased from 152 to 140%, while the air permeability dropped only insignificantly from 3.3 to 3.4 seconds. The adhesiveness without aging was 419 cN. After aging for 1 year the adhesiveness was 462 cN, after 2 years 390 cN, after 3 years 356 cN, after 4 years 413 cN, after 5 years 297 cN, after 6 years 283 cN, and after 7 years 371 cN. When the same bandage was finished according to DE-AS No. 1,491,205 and with a 21% latex content, the extensibility loss was 145%, i.e., the extensibility dropped from 235% in the basic product to 90%. The water holding capacity dropped from 128%, i.e., by 34% and this value is well below that of the basic product. The air permeability dropped from 3.3 seconds form the basic article to 3.9 seconds. The adhesiveness without aging was 277 cN, after 1 year 431 cN, after 2 years 411 cN, after 3 years 235 cN, after 4 years 159 cN, after 5 years 262 cN, after 6 years 214 cN, and after 7 years 139 cN. In order to arrive at comparative values, bandage type 181 was cohesively finished by the dipping process, but the extensibility dropped from 235 to 40%. This value is so low that such a bandage could not be used for a plastic dressing. The latex proportion was 79%.

This led to the low water holding capacity of only 67%, which is well below half that of the basic article. The air permeability dropped from 3.3 seconds in the case of the non-cohesive bandage to 4.2 seconds. The adhesiveness without aging was, despite the high latex percentage of 79%, only 289 cN, after 1 year 176 cN, after 2 years 145 cN, after 3 years 222 cN, after 4 years 159 cN, after 5 years 140 cN, after 6 years 76 cN, and after 7 years 13 cN. It can be concluded from this that, although the latex percentage was extremely high, the adhesiveness had dropped to an extraordinary extent after 2 years, i.e., the cohesive adhesive loses its characteristics and becomes greasy, sticking to skin, hair and articles of clothing.

Thus, an elastic fixing bandage of type 181 made cohesive by the process of the invention has very advantageous values for the water holding capacity, the air permeability, the adhesiveness and the elastic behavior.

As can be gathered from Table 3, the conditions are much the same with type 600 bandages having a basic extensibility of 200%.

4 years 664 cN, after 5 years 541 cN, after 6 years 556 cN, and after 7 years 427 cN.

A type 600 bandage cohesively finished according to DE-AS No. 1,491,205 has a 50% extensibility loss, i.e., the extensibility has dropped from 200 to 150%. The water holding capacity is only 105% compared with the basic article with 134%. Whereas the air permeability of a type 600 bandage cohesively finished according to the process of the invention rose from 7.0 to 7.4 seconds, the time taken to force 10 liters of air through a bandage finished according to DE-AS No. 1,491,205 under the same physical conditions was 9.9 seconds, i.e., there is a considerable increase due to the method. With a latex proportion of 17%, the adhesiveness of a bandage produced according to DE-AS No. 1,491,205 without aging was 435 cN, after 1 year 189 cN, after 2 years 319 cN, after 3 years 402 cN, after 4 years 589 cN, after 5 years 490 cN, after 6 years 478 cN, and after 7 years 389 cN.

In the case of a type 600 bandage cohesively finished according to the dipping process, the extensibility was found to be only 1.5%, i.e., the extensibility drops from 200 to 115% as a result of the cohesive finish. The water holding capacity dropped to the insignificant value of 50%, while the air permeability dropped from 7.0 to 12.5 seconds. Although the latex proportion was 42%, the adhesiveness without aging was 498 cN, after aging for 1 year was only 257 cN, after 2 years 226 cN, after 3 years 196 cN, after 4 years 213 cN, after 5 years 118 cN, after 6 years 117 cN, and after 7 years 107 cN. It should be noted that from the fourth year on, the cohesive character, i.e., the individual turns only adhering to one another and not to the skin, hair or clothing, was lost because at that time, the adhesive became greasy and started to stick to skin, hair and clothing. Thus, with such a permanent elastic compression and support bandage, the cohesive finish thereof by the process of the invention only has an insignificant influence on the water holding capacity, air permeability, etc. The extensibility loss of 200 to 180% is insignificant and, despite pronounced aging, the adhesiveness values are in very favorable ranges.

In summarizing, it can be said that based on the pres-

TABLE 3

| | | | | Technical-Physical Data | | | | | | | |
|---|---|---|---|---|---|---|---|---|---|---|---|
| | | Water- | Air- | | Adhesiveness in cN | | | | | | |
| | Extensibility % % | Latex % | holding Capacity 10l/sec. | permeability aging | Without year | after 1 years | after 2 years | after 3 years | after 4 years | after 5 years | after 6 years | after 7 |
| Bandage 600 basic product | 200 | 0 | 134 | 7.0 | — | — | — | — | — | — | — | — |
| Bandage 600 appliction process | 180 | 15 | 120 | 7.5 | 475 | 390 | 243 | 527 | 664 | 541 | 556 | 427 |
| Bandage 600 according to DE-AS 1,491,205 | 150 | 17 | 105 | 9.9 | 435 | 198 | 319 | 402 | 589 | 490 | 478 | 389 |
| Bandage 600 dipping process | 115 | 42 | 50 | 12.5 | 490 | 257 | 226 | 196 | 213 | 118 | 117 | 107 |

The water holding capacity of such a bandage is 134%. When cohesively finished by the process according to the invention, the same bandage only reveals an extensibility loss of 20%, i.e., the extensibility drops from 200 to 180%. The latex percentage is 15% and the water holding capacity drops from 134 to 120%, while the air permeability rises only from 7.0 to 7.5 seconds. The adhesiveness without aging is 475 cN, after 1 year 390 cN, after 2 years 342 cN, after 3 years 527 cN, after ent examples of types 103, 181, and 600 bandages, it is shown that the cohesive finishing thereof by the process of the invention, the macroscopic values such as extensibility, i.e., elastic behavior, water holding capacity and air permeability only dropped insignificantly. These macroscopic values confirm the microscopic values obtained. As a result of the cohesive finish according to the present process, regardless of the type of bandage involved, the individual particles scarcely impaired the indication range, i.e., the individual particles are located in almost droplet-like manner on the surface of the fabric, especially on the fiber ends of the bandages, and claw into one another between the individual turns. Unlike the bandages produced by the known processes, the individual rubber particles do not cause the weft and warp threads to stick together. Thus, the breathing activity is not made impaired and, consequently, there is no narrowing of the indication range. As a result of the very fine particles and the uniformity of distribution, the formation of heat and moisture chambers between skin and bandage, which are a prerequisite for inflammation foci, is avoided.

With respect to the above-mentioned bandage types 103, 181, and 600, it is pointed out that bandage type 103 is a compression bandage, whose extensibility is 90% as a result of elastic, twisted crepe threads. The twisting of these threads of Nm 50/2 is approximately 2.150, and the threads are arranged in such a way that a thread with an S-twisting direction is followed by a thread with a Z-twisting direction, or two threads with an S-twisting direction are followed by two threads with a Z-twisting direction. The elastic element of the elastic fixing bandage of type 181 is a textured, polyfilic, synthetic thread, followed by two rigid staple fiber or cotton threads.

The type 600 permanent elastic compression bandage contains covered polyurethane or rubber threads, as well as rigid cotton or staple fiber threads in a ratio of 1:1, 1:2, 1:3, 1:4, etc.

The results of the size and percentage distribution of the particles applied to the surface of the bandage are given in Tables 4 to 22.

Figure 5:
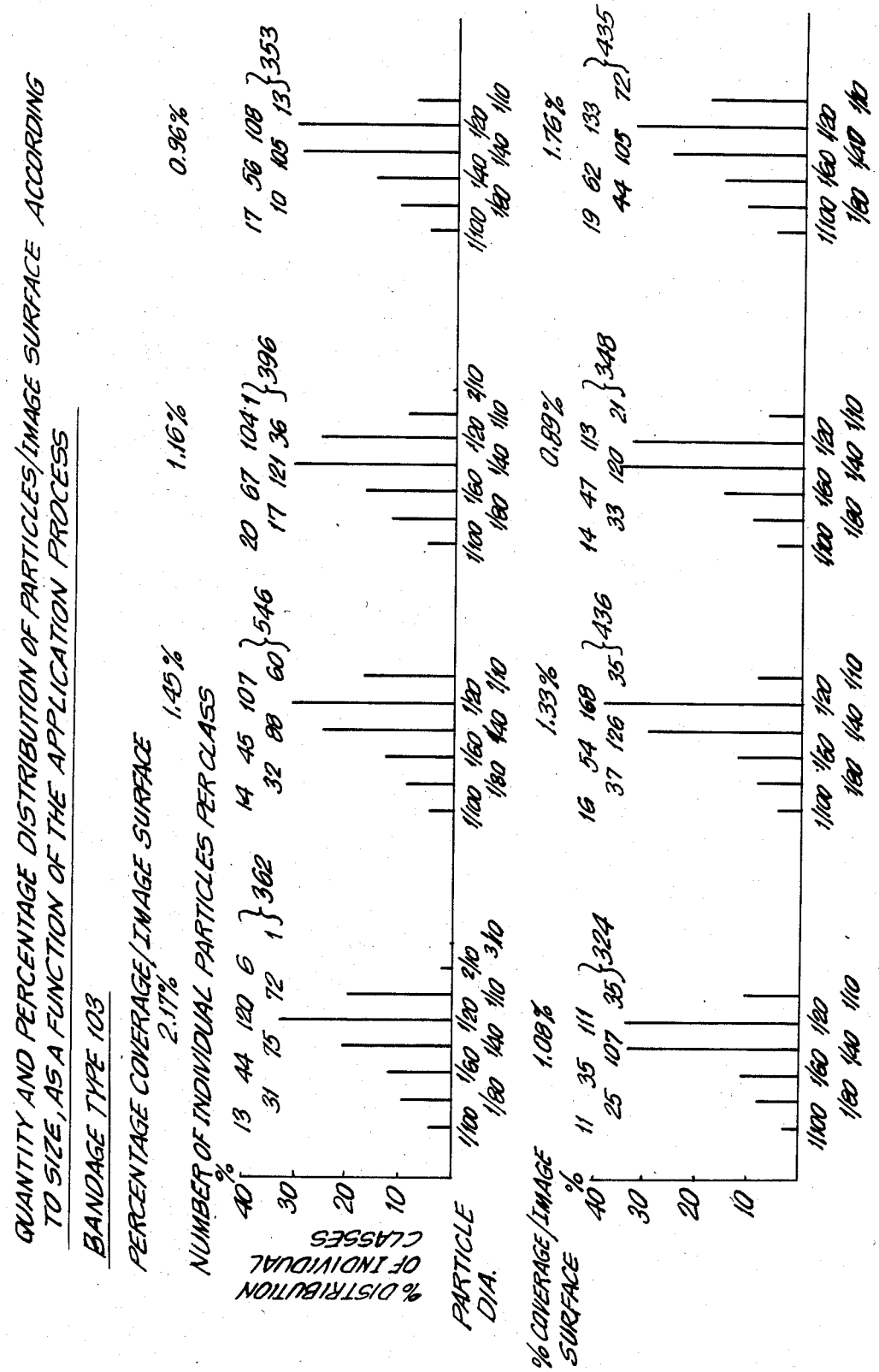
FIGS. 5 and 6 show the size and percentage distribution of the adhesive particles applied to a type 103 bandage by the process of this invention (see examples).
Figure 6:
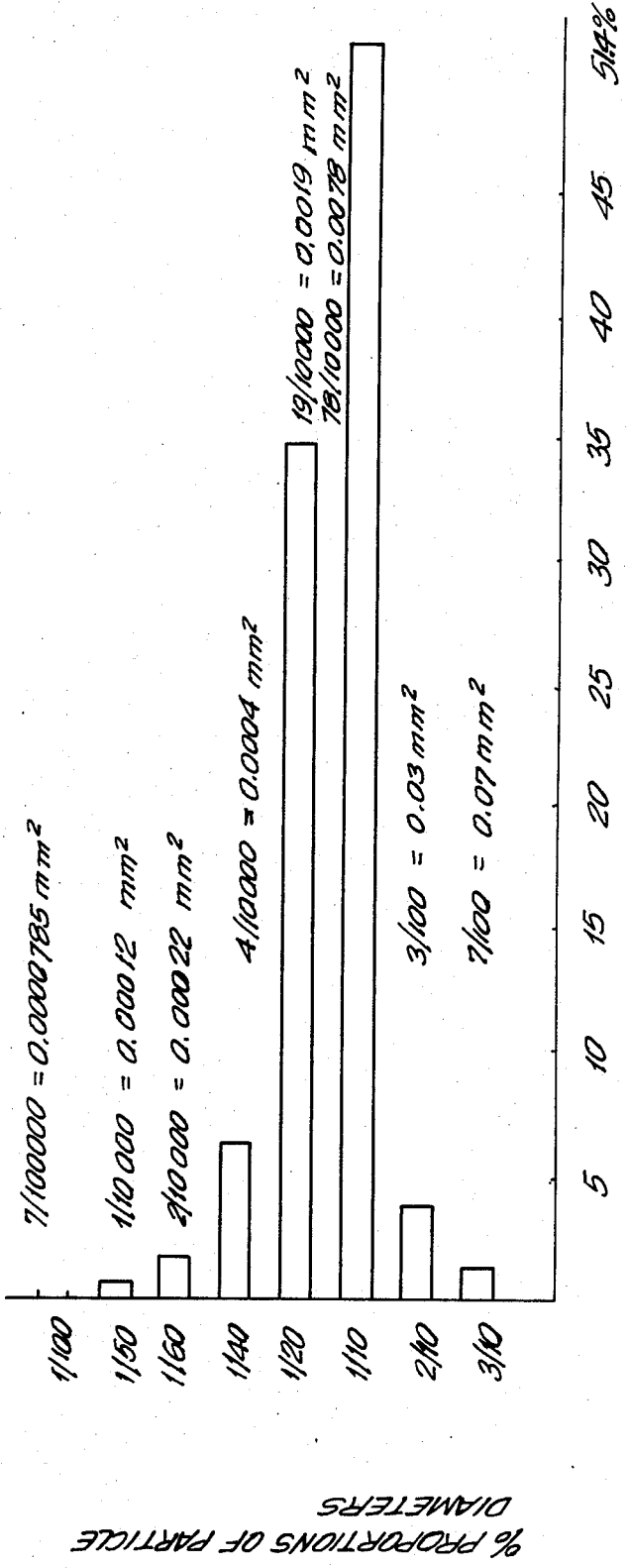

FIGS. 5 and 6 show the size and percentage distribution of the particles applied to a type 103 bandage by the process of the invention and Table 5 shows the percentage area coverage.

Figure 7:
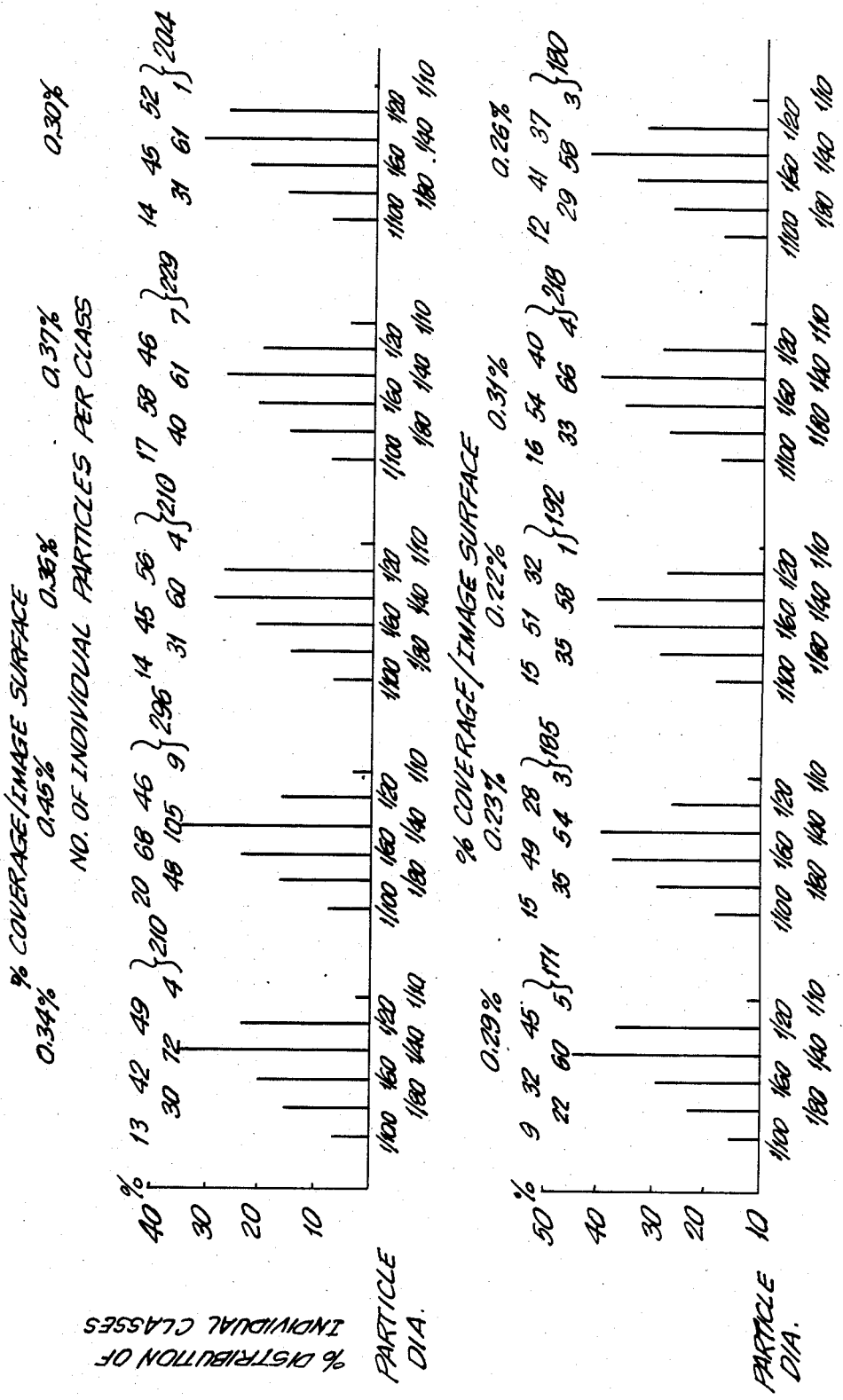
FIGS. 7 and 8 show the size and percentage distribution of the adhesive particles applied to a type 181 bandage by the process of the invention (see examples).
Figure 8:
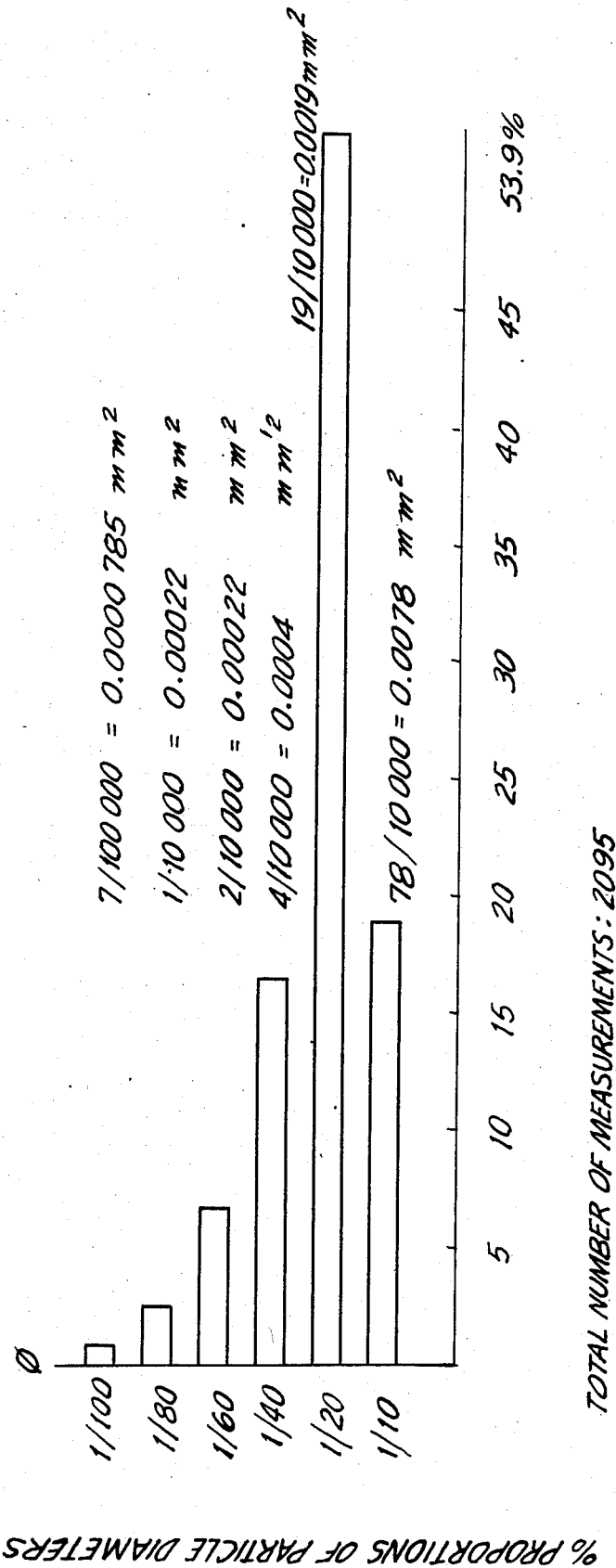

FIGS. 7 and 8 show the size and percentage distribution of the particles applied to a type 181 bandage by the process of the invention and Table 6 shows the percentage area coverage.

Figure 9:
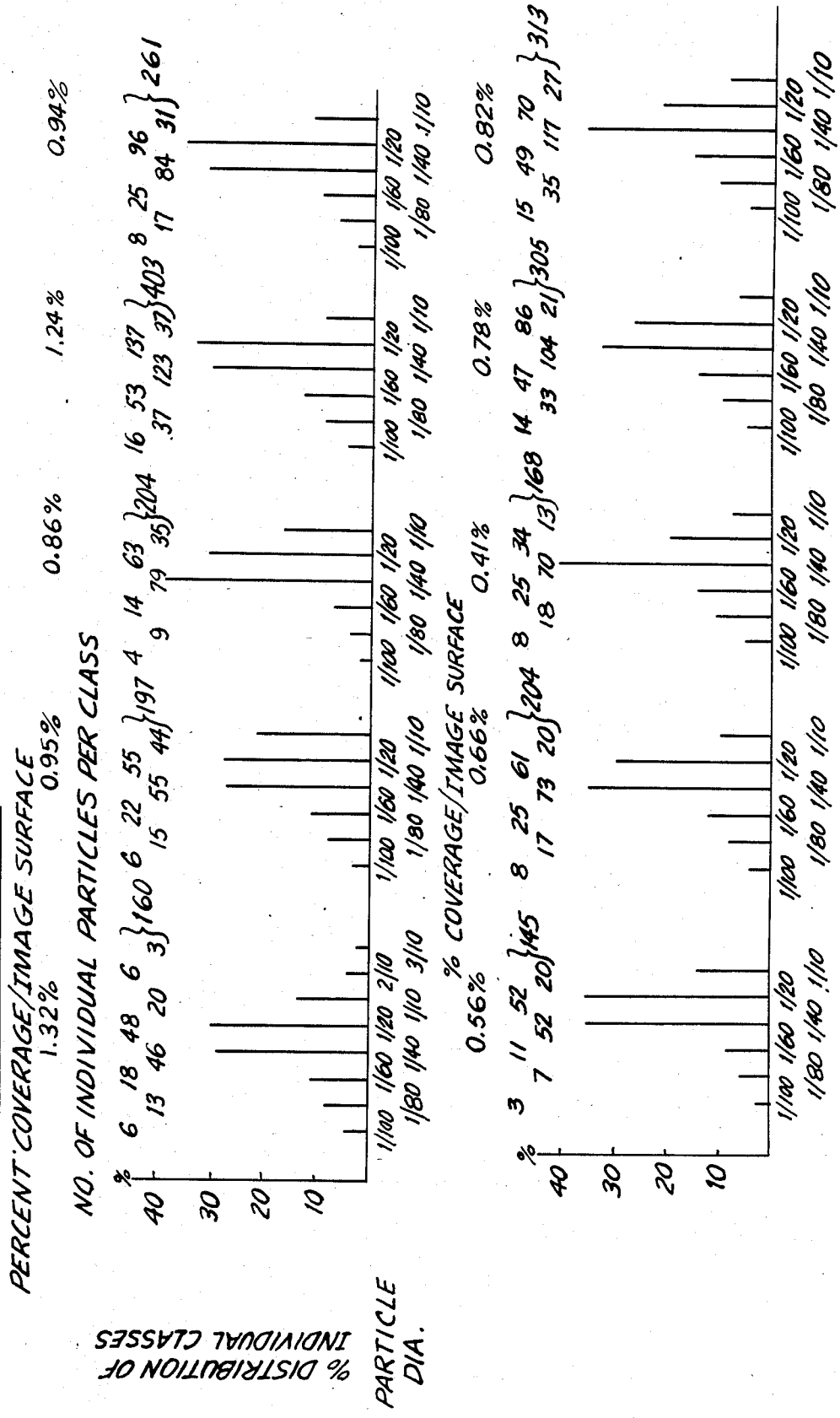
FIGS. 9 and 10 show the size and percentage distribution of the adhesive particles applied by the process of the invention (see examples).
Figure 10:
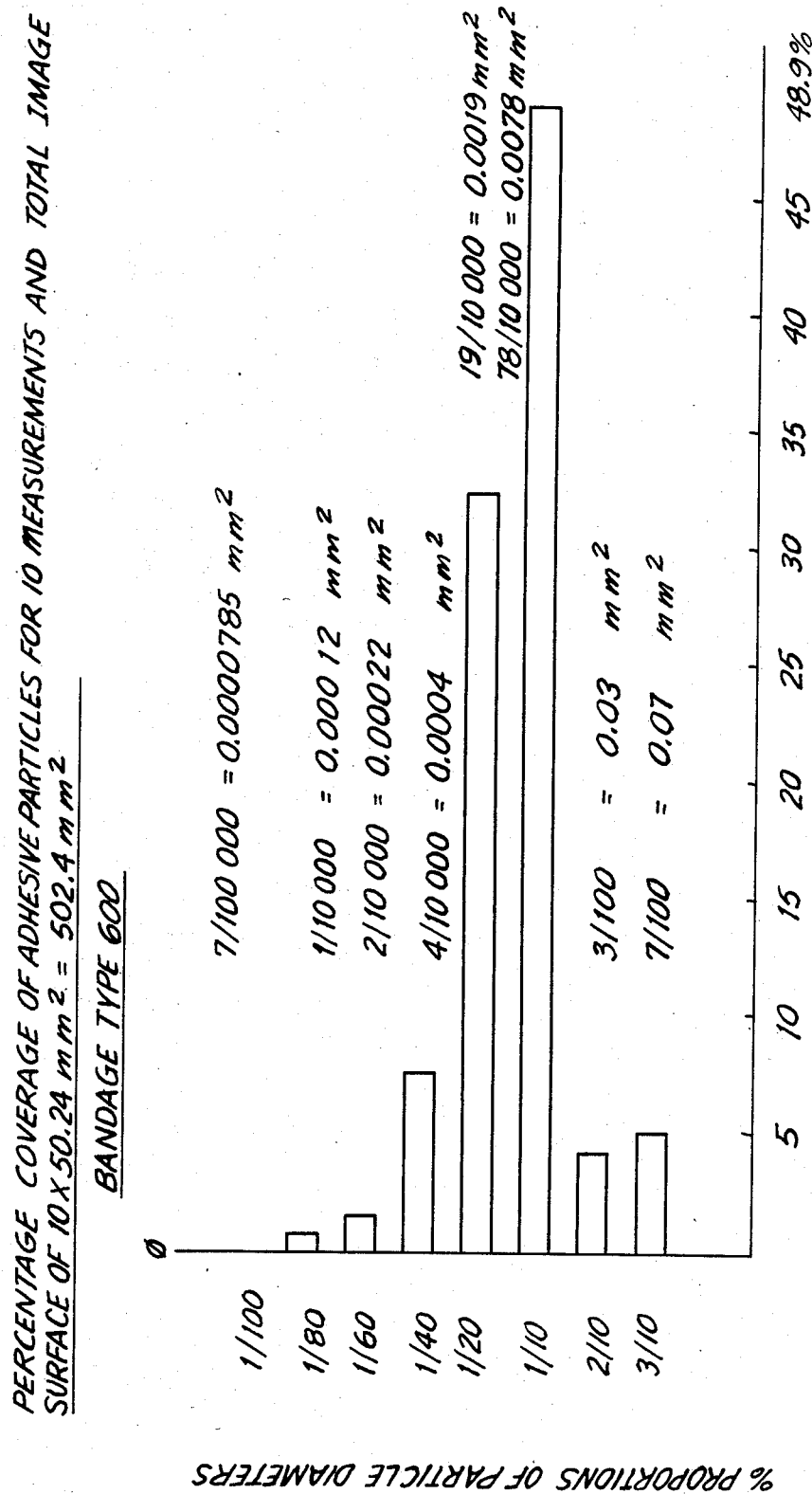

FIGS. 9 and 10 show the size and percentage distribution of the particles applied by the process of the invention to a type 600 bandage and Table 7 shows the percentage area coverage.

Figure 11:
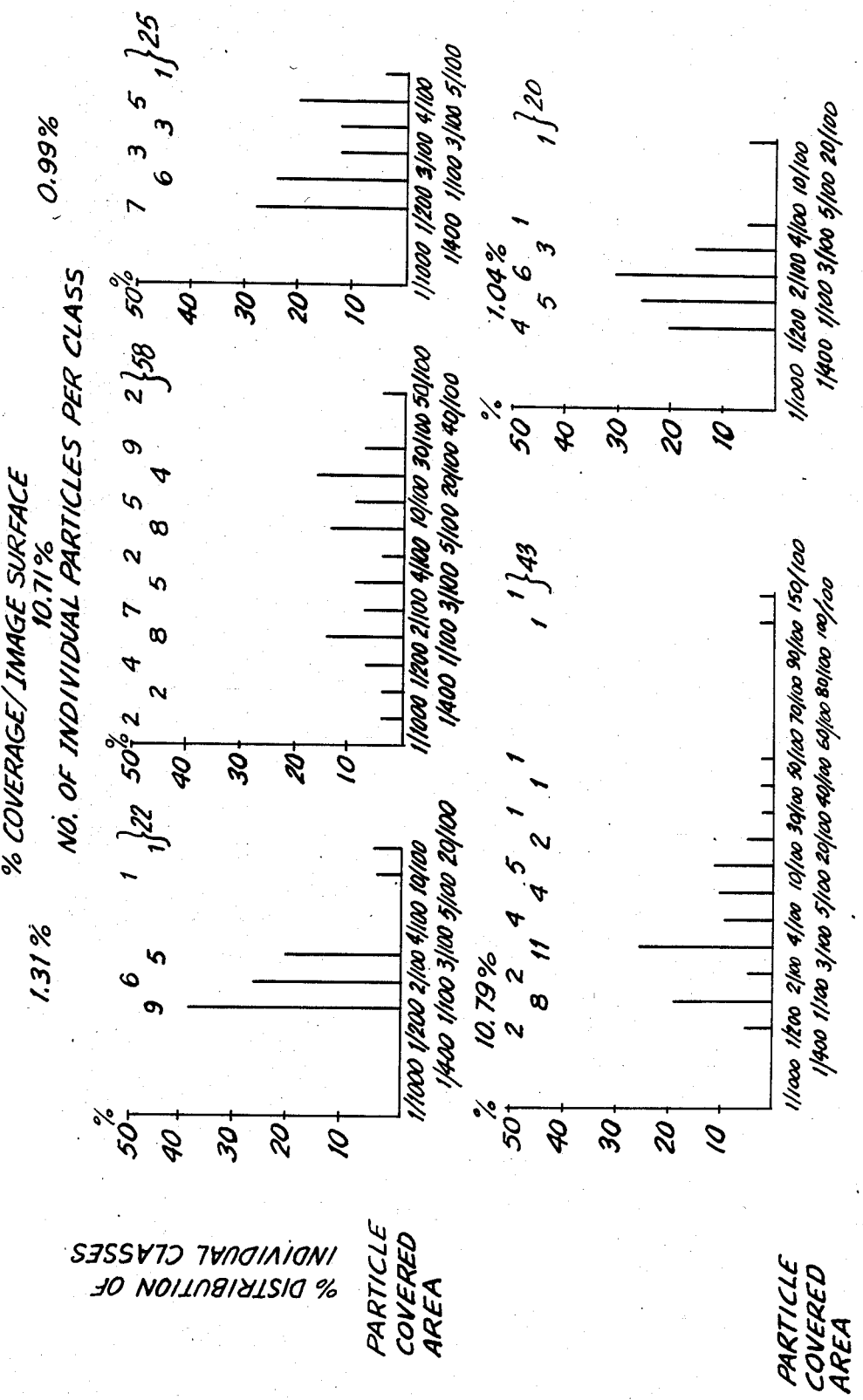
FIGS. 11, 12 and 13 show the size and percentage distribution of the particles applied to a type 181 bandage produced in accordance with prior art DE-AS No. 1,491,205 (see examples).
Figure 12:
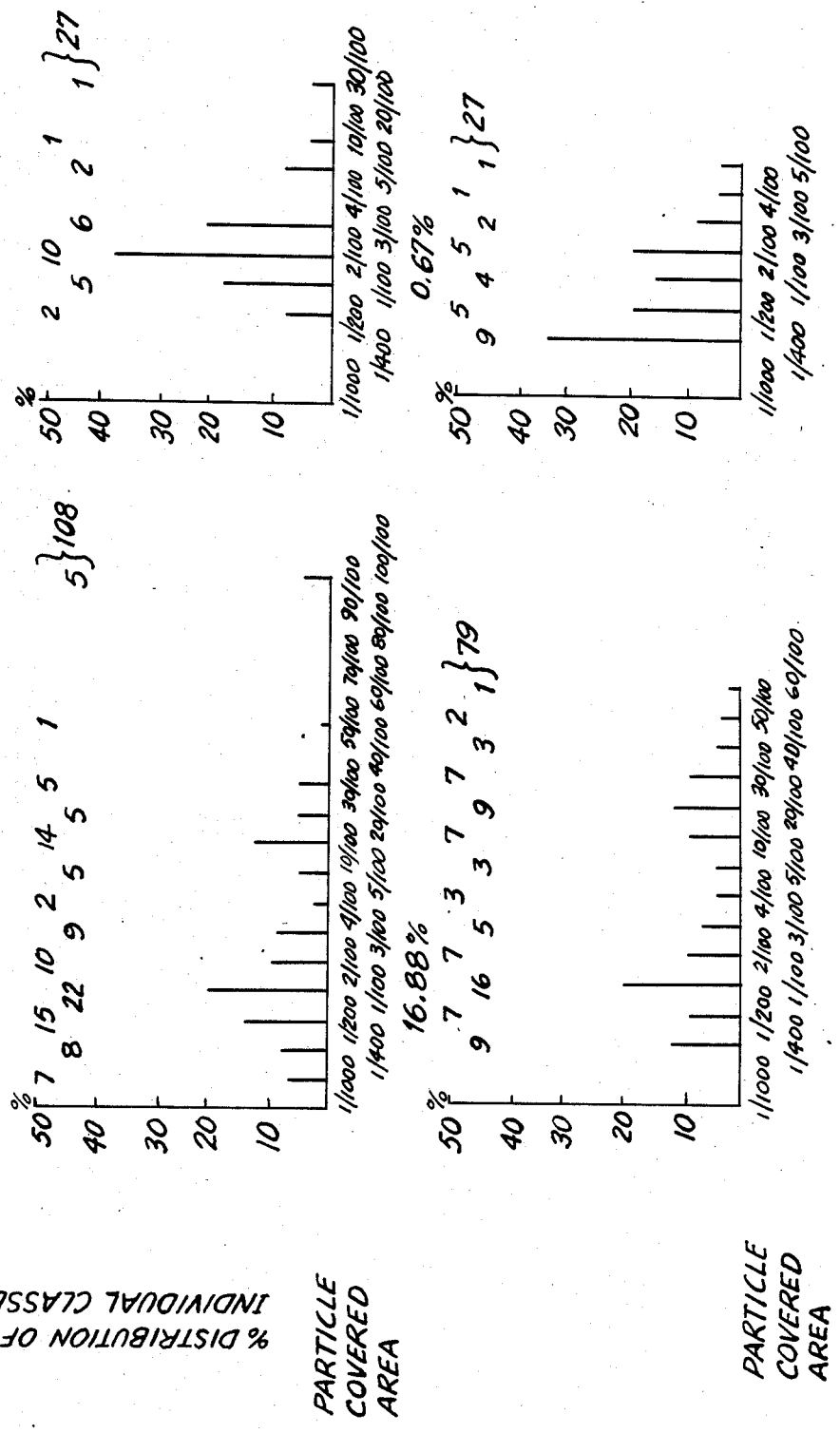
Figure 13:
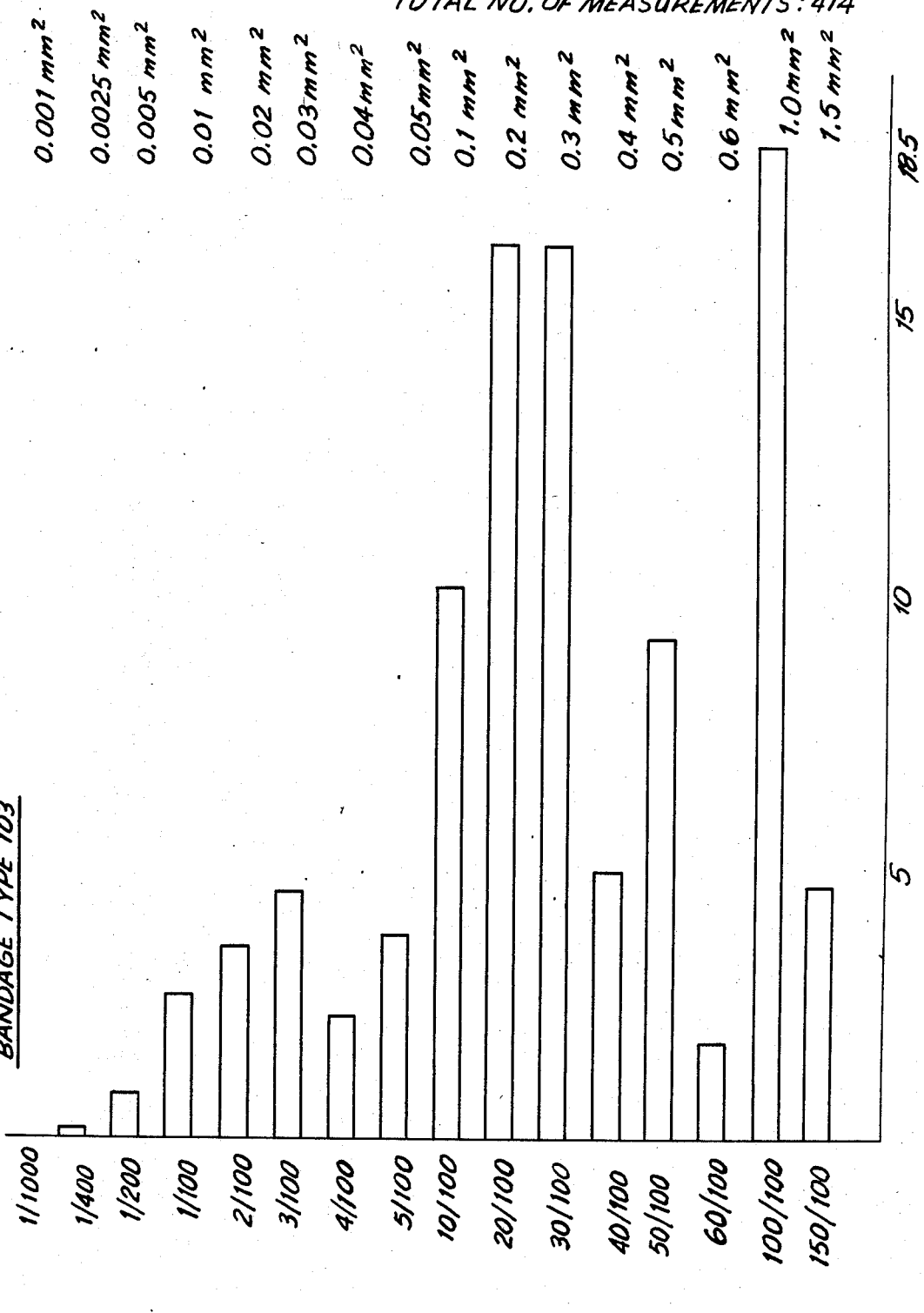

FIGS. 11, 12 and 13 show the size and percentage distribution of the particles applied to a type 103 bandage produced according to DE-AS No. 1,491,205 and Table 8 shows the percentage area coverage.

FIGS. 14, 15, 16 and 17 show the size and percentage distribution of the particles applied to a type 181 bandage produced according to DE-AS No. 1,491,205 and Table 9 shows the percentage area coverage.

The different cohesive finishing of bandages of type 103, 181, and 600 is explained in greater detail by means of FIGS. 5 to 17 and Tables 5 to 9.

TABLE 4

Quantity and percentage distribution of particles/image surface according to size, as a function of the application process
Bandage type 103
Percentage coverage of the microscopically visible image surface of 50.24 mm$^2$ determined by graph paper.
Calculation Example:

| particle dia. | calculated particle size | coverage | mm$^2$ |
|---|---|---|---|
| 1/100 | 1/200 × 1/200 × 3.14 = | 0.0000785 × 13 = | 0.0010 mm$^2$ |
| 1/80 | 1/160 × 1/160 × 3.14 = | 0.00012 × 31 = | 0.0037 mm$^2$ |
| 1/60 | 1/120 × 1/120 × 3.14 = | 0.00022 × 44 = | 0.0097 mm$^2$ |
| 1/40 | 1/80 × 1/80 × 3.14 = | 0.00040 × 75 = | 0.03 mm$^2$ |
| 1/20 | 1/40 × 1/40 × 3.14 = | 0.00196 × 120 = | 0.235 mm$^2$ |
| 1/10 | 1/20 × 1/20 × 3.14 = | 0.0078 × 72 = | 0.562 mm$^2$ |
| 2/10 | 1/10 × 1/10 × 3.14 = | 0.03 × 6 = | 0.18 mm$^2$ |
| 3/10 | 3/20 × 3/20 × 3.14 = | 0.07 × 1 = | 0.07 mm$^2$ |
| | | | 1.0914 mm$^2$ |
| | | image surface 50.24 mm$^2$ = | 2.17% |

All graphs were based on this calculation example.

TABLE 5

Application Process
Bandage Type 103

Total surface area of 123 measurements (0.18%) for a magnitude of 0.0000785 mm$^2$ = 0.00967 mm$^2$
Total surface area of 288 measurements (0.64%) for a magnitude of 0.0001200 mm$^2$ = 0.03456 mm$^2$
Total surface area of 412 measurements (1.67%) for a magnitude of 0.0002200 mm$^2$ = 0.09064 mm$^2$
Total surface area of 847 measurements (6.23%) for a magnitude of 0.0004000 mm$^2$ = 0.33880 mm$^2$
Total surface area of 964 measurements (34.76%) for a magnitude of 0.0019600 mm$^2$ = 1.88940 mm$^2$
Total surface area of 358 measurements (51.37%) for a magnitude of 0.0078000 mm$^2$ = 2.79240 mm$^2$
Total surface area of 7 measurements (3.86%) for a magnitude of 0.0300000 mm$^2$ = 3.86000 mm$^2$
Total surface area of 1 measurements (1.29%) for a magnitude of 0.0700000 mm$^2$ = 0.07000 mm$^2$
Total coverage: 3000 particles      Total surface area: 5.43547 mm$^2$
Size of complete stereo image surface of 8 stereo images: 401.92 mm$^2$
Percentage of covered surface of total surface area: 1.35%

TABLE 6

Application Process
Bandage Type 181

Total surface area of 145 measurements (0.72%) for a magnitude of 0.0000785 mm$^2$ = 0.01138 mm$^2$
Total surface area of 339 measurements (2.59%) for a magnitude of 0.0001200 mm$^2$ = 0.04068 mm$^2$
Total surface area of 485 measurements (6.79%) for a magnitude of 0.0002200 mm$^2$ = 0.10670 mm$^2$
Total surface area of 655 measurements (16.67%) for a magnitude of 0.0004000 mm$^2$ = 0.26200 mm$^2$ TABLE 6-continued Application Process
Bandage Type 181

Total surface area of 432 measurements (53.87%) for a magnitude of 0.0019600 mm$^2$ = 0.84672 mm$^2$
Total surface area of 39 measurements (19.36%) for a magnitude of 0.0078000 mm$^2$ = 0.30420 mm$^2$
Total coverge: 2095 particles   Total surface area: 1.57168 mm$^2$
Size of complete stereo image surface of 10 stereo images: 502.40 mm$^2$
Percentage of covered surface of total surface area: 0.31%

TABLE 7

Application Process
Bandage Type 600

Total surface area of 87 measurements (0.16%) for a magnitude of 0.0000785 mm$^2$ = 0.00683 mm$^2$
Total surface area of 202 measurements (0.57%) for a magnitude of 0.0001200 mm$^2$ = 0.02424 mm$^2$
Total surface area of 289 measurements (1.49%) for a magnitude of 0.0002200 mm$^2$ = 0.06358 mm$^2$
Total surface area of 803 measurements (7.52%) for a magnitude of 0.0004000 mm$^2$ = 0.32120 mm$^2$
Total surface area of 702 measurements (32.21%) for a magnitude of 0.0196000 mm$^2$ = 1.37592 mm$^2$
Total surface area of 268 measurements (48.93%) for a magnitude of 0.0078000 mm$^2$ = 2.09040 mm$^2$
Total surface area of 6 measurements (4.21%) for a magnitude of 0.0300000 mm$^2$ = 0.18000 mm$^2$
Total surface area of 3 measurements (4.92%) for a magnitude of 0.0700000 mm$^2$ = 0.21000 mm$^2$
Total coverage: 2360 particles   Total surface area: 4.27217 mm$^2$
Size of complete stereo image surface of 10 stereo images: 502.40 mm$^2$
Percentage of covered surface of total surface area: 0.85%

TABLE 8

According to DE-AS 1,491,205 - Bandage Type 103

Total surface area of 9 measurements (0.028%) for a magnitude of 0.0001 mm$^2$ = 0.009 mm$^2$
Total surface area of 28 measurements (0.216%) for a magnitude of 0.0025 mm$^2$ = 0.070 mm$^2$
Total surface area of 51 measurements (0.785%) for a magnitude of 0.0050 mm$^2$ = 0.255 mm$^2$
Total surface area of 83 measurements (2.556%) for a magnitude of 0.01 mm$^2$ = 0.830 mm$^2$
Total surface area of 56 measurements (3.449%) for a magnitude of 0.02 mm$^2$ = 1.120 mm$^2$
Total surface area of 49 measurements (4.527%) for a magnitude of 0.03 mm$^2$ = 1.470 mm$^2$
Total surface area of 18 measurements (2.217%) for a magnitude of 0.04 mm$^2$ = 0.720 mm$^2$
Total surface area of 24 measurements (3.695%) for a magnitude of 0.05 mm$^2$ = 1.200 mm$^2$
Total surface area of 33 measurements (10.162%) for a magnitude of 0.1 mm$^2$ = 3.300 mm$^2$
Total surface area of 27 measurements (16.629%) for a magnitude of 0.2 mm$^2$ = 5.400 mm$^2$
Total surface area of 18 measurements (16.629%) for a magnitude of 0.3 mm$^2$ = 5.400 mm$^2$
Total surface area of 4 measurements (4.927%) for a magnitude of 0.4 mm$^2$ = 1.600 mm$^2$
Total surface area of 6 measurements (9.238%) for a magnitude of 0.5 mm$^2$ = 3.000 mm$^2$
Total surface area of 1 measurements (1.848%) for a magnitude of 0.6 mm$^2$ = 0.600 mm$^2$
Total surface area of 6 measurements (18.476%) for a magnitude of 1.0 mm$^2$ = 6.000 mm$^2$
Total surface area of 1 measurements (4.619%) for a magnitude of 1.5 mm$^2$ = 1.500 mm$^2$
Total coverage: 414   Total surface area: 32.474 mm$^2$
Size of complete stereo image surface of 9 stereo images: 452.16 mm$^2$
Percentage of covered surface of total surface area: 7.18%

TABLE 9

According to DE-AS 1,491,205 - Bandage Type 181

Total surface area of 9 measurements (0.43%) for a magnitude of 0.01 mm$^2$ = 0.08 mm$^2$
Total surface area of 16 measurements (1.72%) for a magnitude of 0.02 mm$^2$ = 0.32 mm$^2$
Total surface area of 16 measurements (2.58%) for a magnitude of 0.03 mm$^2$ = 0.48 mm$^2$
Total surface area of 15 measurements (3.22%) for a magnitude of 0.04 mm$^2$ = 0.60 mm$^2$
Total surface area of 40 measurements (10.74%) for a magnitude of 0.05 mm$^2$ = 2.00 mm$^2$
Total surface area of 5 measurements (2.15%) for a magnitude of 0.08 mm$^2$ = 0.40 mm$^2$
Total surface area of 64 measurements (34.35%) for a magnitude of 0.10 mm$^2$ = 6.40 mm$^2$
Total surface area of 24 measurements (19.32%) for a magnitude of 0.15 mm$^2$ = 3.60 mm$^2$
Total surface area of 21 measurements (22.54%) for a magnitude of 0.20 mm$^2$ = 4.20 mm$^2$
Total surface area of 1 measurements (1.34%) for a magnitude of 0.25 mm$^2$ = 0.25 mm$^2$
Total surface area of 1 measurements (1.61%) for a magnitude of 0.30 mm$^2$ = 0.30 mm$^2$
Total coverage: 211   Total surface area: 16.962 mm$^2$
Size of complete stereo image surface of 10 stereo images: 502.4 mm$^2$
Percentage of covered surface of total surface area: 3.38%

As can be gathered from the graphs of Table 4 and FIGS. 5 and 6, the number of counted particles per image detail (50.24 mm$^2$) is between 350 and 450. 3000 particles were recorded for 8 image details 8 times 50.25 mm$^2$ =401.94 mm$^2$. Most of the particles and specifically approximately 86% were between 20/10,000 and 78/10,000 mm$^2$. The calculation of the surface area of 3000 particles gave 5.43 times 8 =401.9 mm$^2$, representing a percentage area coverage of 1.35%. This refers to a type 103 bandage. However, the same applies for a type 181 bandage. FIGS. 7 and 8 show that the number of particles was about 200, so that the total number of particles of the ten image areas of 502.4 mm$^2$ is 2095. The greatest percentage of the particles were between 20/10,000 and 78/10,000. The particles of a magnitude of 20/10,000 mm$^2$ represented 53.9%. Thus, from the total number of particles, a coverage of 1.57 mm$^2$, corresponding to a percentage area coverage of 0.31 is calculated for 502.4 mm$^2$.

The same picture is obtained for an identical cohesive finish with a type 600 bandage according to FIGS. 9 and 10, where the number of particles per image detail is between 51 and 400. 2,360 particles were counted for the 10 image details, the largest proportion being at 20/10,000 mm$^2$ and 78/10,000 mm$^2$. Thus, there is an overall coverage of 4.3 mm$^2$, corresponding to a percentage surface coverage of 0.85% for the 2,360 particles with a total image surface of $10 \times 50.24$ mm$^2 = 502.4$ mm$^2$. The same values are shown in the technical-physical data of Tables 1 to 3. They show that the extensibility of a finished type 103 bandage has only dropped by 10% compared with the basic article, i.e., from 95 to 85%. The water holding capacity dropped from 70% in the basic article to 66%, while the air permeability for the same bandage rose from 7 seconds to 8.6 seconds. In the case of a latex proportion of only 15%, the energy of adhesion both with and without aging, no matter whether it was after 1 year or after 7 years, was much higher than in the cohesive bandages treated by the dipping process or DE-AS No. 1,491,205.

The same picture is repeated for type 181 bandages. As a result of the fine particles, the water holding capacity only dropped from 152 to 140%, compared with the basic article. The air permeability for forcing 10 liters of air through the fabric under identical physical conditions only rose by 0.1%. With regard to the adhesiveness, both with and without aging, with the cohesive finish according to the present process, much higher values are obtained than with the previously described cohesively finished bandages according to the dipping process or according to DE-AS No. 1,491,205. The order of magnitude and distribution are also shown in the technical-physical data of a type 600 bandage. Thus, the extensibility only dropped from 200 to 180% compared with a non-cohesively finished bandage. The water holding capacity dropped from 137 to 120%, while the air permeability rose from 7.0 to 7.5 seconds. In the case of a latex proportion of 15%, values were obtained for the adhesiveness both with and without aging which are well above the values obtained with a cohesive finish by the dipping or roller application processes.

Figure 14:
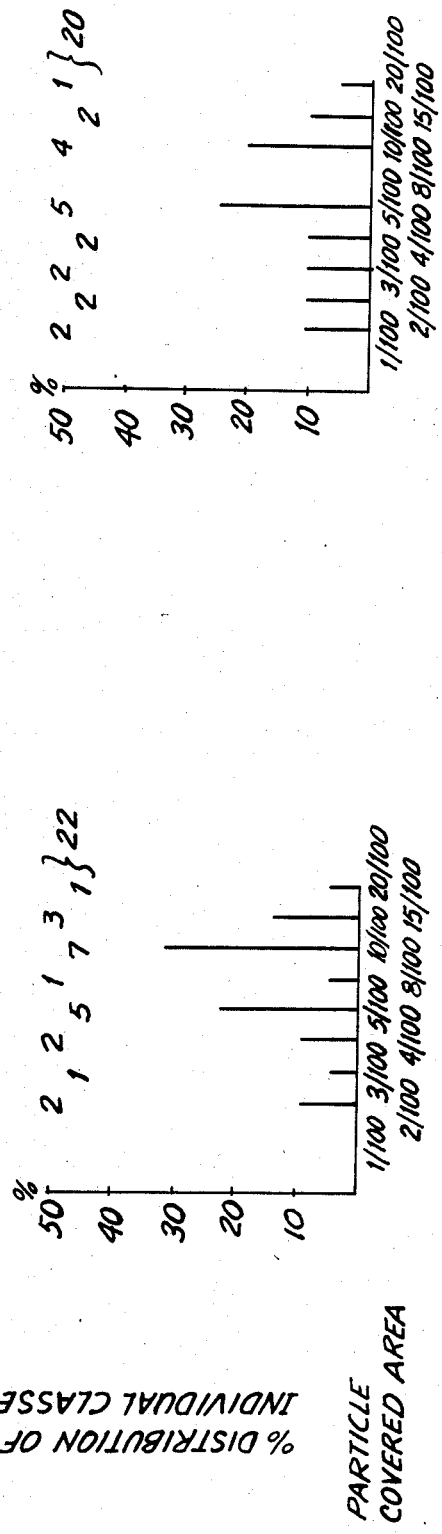
FIGS. 14, 15, 16 and 17 show the size and percentage distribution of the adhesive particles applied to a type 181 bandage produced in accordance with DE-AS No. 1,491,205 (see examples).
Figure 14:
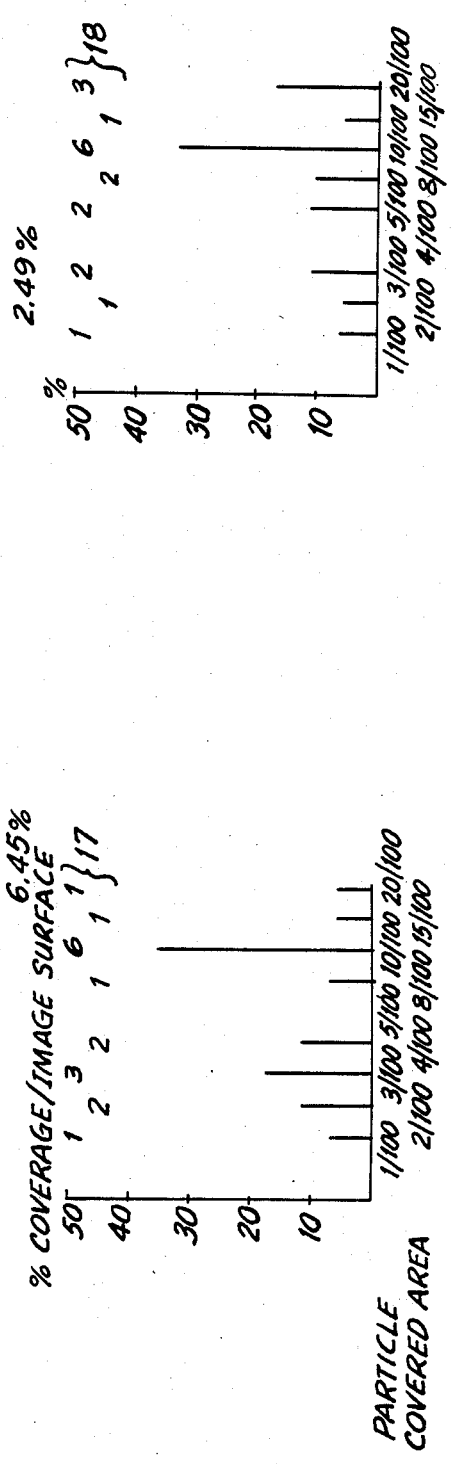
Figure 15:
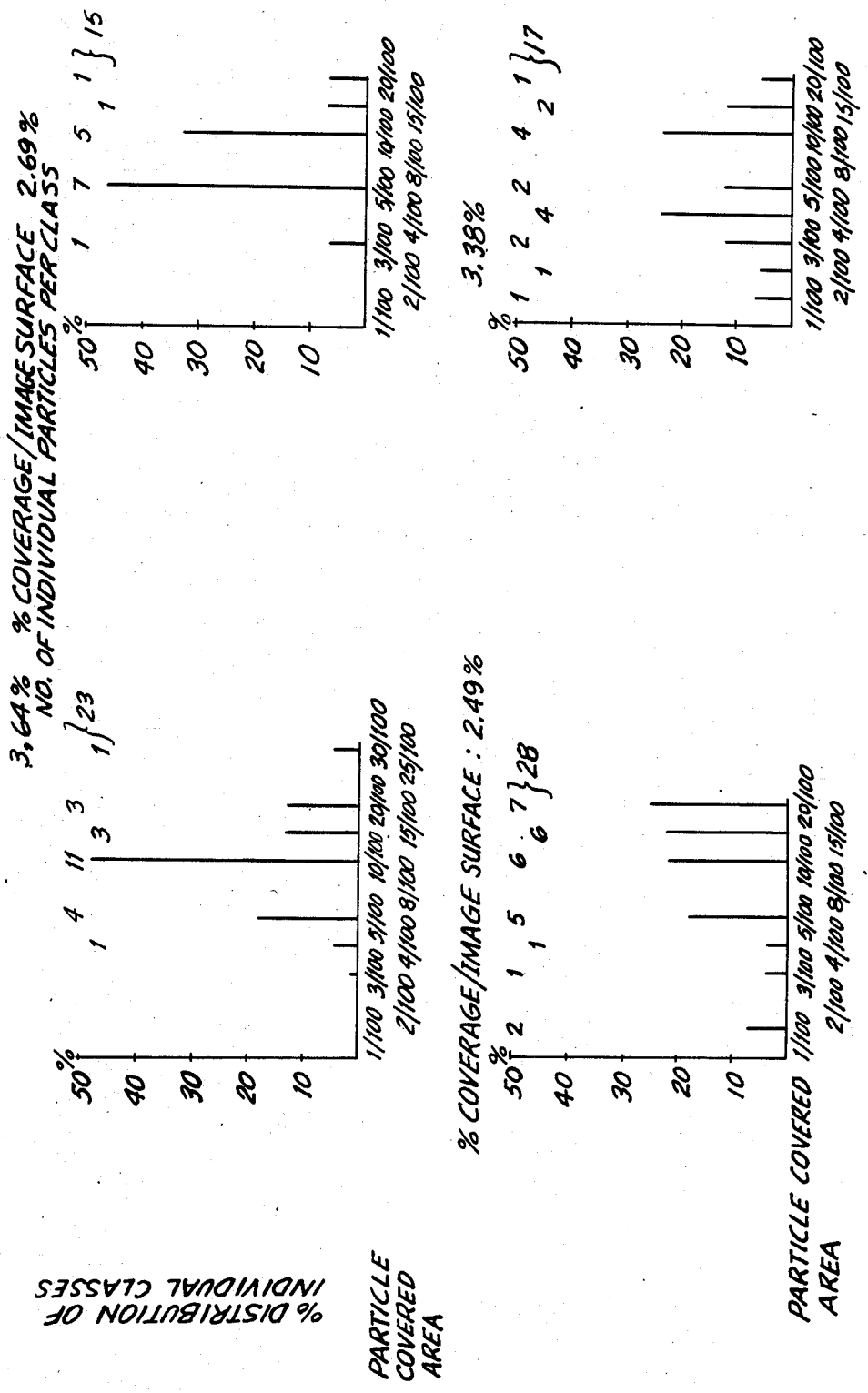
Figure 16:
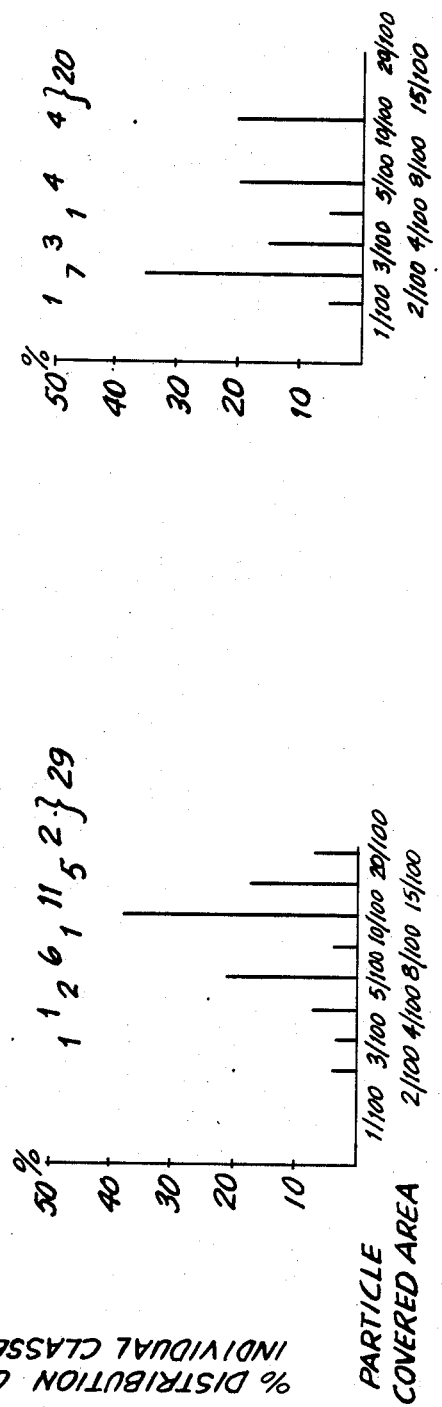

Admittedly, with a bandage having a cohesive finish according to DE-AS No. 1,491,205, the indication range is not limited to the same extent as with bandages cohesively finished by the dipping process, but in a number of areas of said bandage, the breathing activity of the groups of fibers is negatively influenced to a considerable extent, i.e., the bridge formation between skin and external air is reduced. The number of particles and the percentage distribution thereof on the bandage surface are determined according to FIGS. 14, 15 and 16. The percentage coverage is determined by adhesive particles for 10 measurements and therefore, for a natural total surface area of 502.4 mm$^2$ according to classes in 211 measurements (FIG. 17), together with the percentage area coverage for a natural surface of fibers 502.4 mm$^2$ (Table 9). FIGS. 14 and 15 show that the number of particles per image surface is approximately 20. The size of the particles is mainly 10/100, 15/100 and 20/100 mm$^2$. Thus, for a total natural surface of 502.4 mm$^2$ and 211 measurements, there is a total coverage of 16.9 mm$^2$, corresponding to a percentage coverage of 3.38%.

Figure 17:
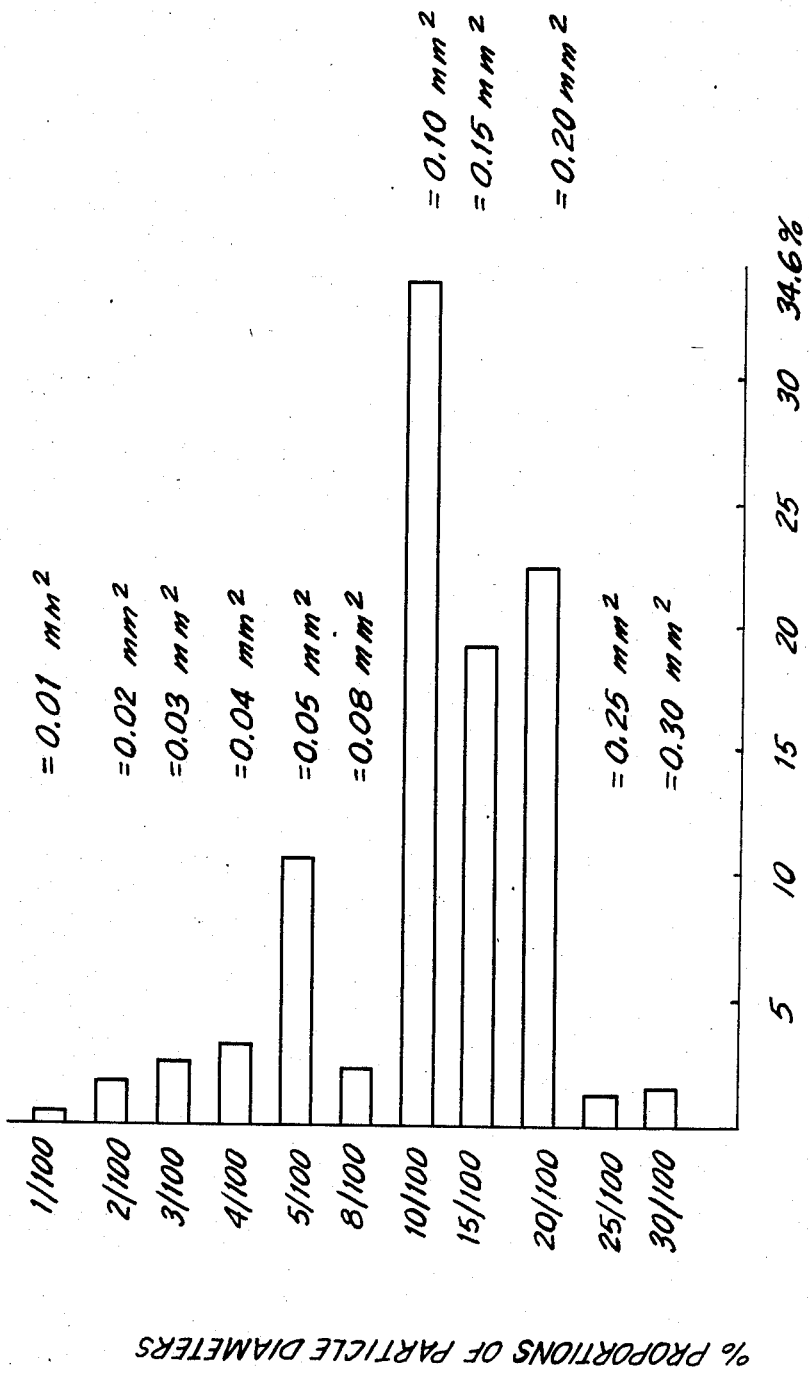

The same picture is obtained for a type 103 bandage cohesively finished according to the process of DE-AS No. 1,941,205. Although the number of particles per surface is somewhat higher, the distribution is of a very random nature, which is apparent from the strip-arrangement of the adhesive coating (FIGS. 11 and 12). The total number of particles was 414 for a natural image size of 452.16 mm$^2$. Here again and in accordance with FIG. 13, most of the particles were of sizes of 10/100, 20/100, 30/100, 40/100, 50/100 and 60/100 and even 1 mm. Thus, as is shown by FIG. 17, there is a total coverage area of 32.47 mm$^2$ with a natural surface of 452.16 mm$^2$, corresponding to a percentage coverage of 7.18%.

Thus, the particles applied to the bandage by the aerosol process according to the invention are 100 to 1000 times smaller than the particles of a bandage cohesively finished according to DE-AS No. 1,491,205. It can be concluded from the particle size of bandages according to the present process and according to that of bandages with a cohesive finish according to DE-AS No. 1,491,205 that the number of particles according to the present process is 10 time higher than with the known construction. Despite the large number of particles after the cohesive finish of the bandages according to the present process, the percentage area coverage is 6 to 7 times lower as compared with a bandage produced according to DE-AS No. 1,491,205, while the adhesiveness is greater. It is also pointed out and this is shown by the graph, that the distribution of the particles is extremely uniform. Referring to the technical-physical data of Tables 1 to 3 and comparing said data, it is clear that the individual bandages of types 103, 181, and 600 have been detrimentally affected with regard to the extensibility, water holding capacity, air permeability and aging. This deterioration, compared with the basic article, is least in the case of bandages cohesively finished according to the present process and with maximum adhesiveness, but increases to a very considerable extent in the case of bandages according to DE-AS No. 1,491,205, with the same latex percentage. The data for the water holding capacity and air permeability were of a very inferior nature in the case of bandages cohesively finished by the dipping process and, in fact, the water holding capacity was 2 to 3 times lower than with the basic article. Much the same applies regarding the air permeability which dropped very considerably due to the high rubber percentage and, in fact, the passage time rose from 7.0 to 12.5 seconds. Although the rubber percentage for the dipping process was 4 to 5 times higher than that in the process according to the invention, the adhesiveness data are much lower.

In summary, it can be stated that as a result of the cohesive finish according to the present process, the particles are so finely and uniformly distributed that in spite of the high adhesiveness, the factors necessary for the healing process, such as, the breathing activity, etc., are in no way impaired and no hot and moist chambers were found. Thus, the superiority of a bandage produced according to the inventive process is established.

As a result of the longitudinal, transverse, and longitudinal/transverse elasticity of the bandages and due to the ultra-fine arrangement of the rubber particles, it is possible to produce plastic and slide-proof, as well as elastic fixing dressings for all parts of the body, even when they have a very small radius, without losing air circulation, moisture absorption and the bridge formation for moisture and water, so that there is no build up of heat and moisture which could provide foci for infection.

With the present invention, a rigid or elastic bandage is obtained wherein both sides are covered extremely finely and uniformly with rubber particles. These result in a high cohesive force so that the individual layers of the bandage are held together and slipping is minimized.

Even so, however, the bandage layers adhere only to themselves and not to the skin, hair or clothing. Moreover, a bandage prepared in such a way possesses water vapor permeability and air permeability, as well as the ability to absorb secretions. Also, if the fabric of the bandage is elastic, the adhesive does not interfere with the elastic properties. Thus, for example, the accumulation of heat and moisture chambers which generally are feared because they can cause infection, are avoided with the present invention. Due to this cohesive embodiment of the bandage of the present invention, after the bandage has been placed, the individual layers of the bandage are securely held and do not slip until they are removed.

The use of an application quantity of rubber which is as small as possible, i.e., in an order of magnitude of 10 to 40 g/m$^2$, is sufficient. The individual particles should be very finely and uniformly distributed over both sides of the bandage surface so that a strong cohesiveness results between the individual layers, regardless of how they are arranged. Additionally, the fiber groups should not adhere to themselves or to one another. The uniformly distributed small particles provide a genuine tooth-like connection without significantly reducing the breathing activity of the fabric. The rubber particles which are applied to the bandage surfaces do not form a continuous sticky coating which penetrates into the interior of the bandage. Thus, the individual particles do not affect the physical behavior of the bandage, such as, for instance, elasticity, reversible energy capacity or breathing activity and the like. In addition, there is no impairment of the elastic behavior of the bandage.

A cohesive adhesive is applied on the surface of the fabric in the finest distribution in accordance with an aerosol method, so that the permeability to air and water does not suffer from the cohesive design of the bandages. Only woven or knitted, highly elastic bandages are used as carrier material. Non-woven fabrics are not used. Cohesively designed bandages do not adhere to skin and hair as do adhesive bandages; rather, the individual bandage layers adhere to each other.

We claim:

1. A cohesive bandage comprising a fabric having weft and warp threads forming a porous structure and having projecting fiber ends, an amount of adhesive particles bonded to the projecting fiber ends on both surfaces of the fabric, said particles being of a size distribution and amount sufficient to provide adhesion between overlying bandage surfaces without substantially reducing the porosity and elasticity of the fabric.

2. Cohesive, rigid or elastic bandage which only adheres to itself and not to skin, hair and clothing, for fixing dressings, compression dressings and support dressings and permanently elastic compression and support dressings for medical purposes, wherein the bandage has bonded to both sides a cohesive substance, said bandage consisting of a web of weft and warp threads, and having fiber ends projecting from said web, said cohesive substance being fine particles of a size of 0.0000785 to 0.07 mm$^2$ of an adhesive, bonded to said fiber ends on both sides of the web in a uniform distribution of 1,000 to 5,000 particles per approximately 500 mm$^2$ in an application quantity in the order of magnitude of 10 to 40 g/m$^2$, wherein there is substantially no reduction in the porosity and elasticity of the fabric.

3. The bandage of claim 2 wherein the application quantity is from 15 to 20 g/m$^2$.

4. The bandage of claim 2 wherein the adhesive substance is rubber.

5. A process for producing a cohesive, self-adhesive, rigid or elastic bandage which does not adhere to the skin, hair and articles of clothing for fixing, compression and support dressings and permanent elastic compression and support dressings for medical purposes, comprising applying an adhesive to both sides of a flat bandage formed from a woven fabric, and having fiber ends projecting from said fabric, said adhesive being applied uniformly to said fiber ends as an aerosol and in a distribution of about 1,000 to 5,000 particles per 500 mm$^2$ of bandage and a quantity of 10 to 40 g/m$^2$ of bandage without substantially reducing the porosity and elasticity of the fabric.

6. The process of claim 5 wherein the quantity of adhesive applied is from about 15 to 20 g/m$^2$.

7. A bandage obtained by the process of claim 5.

8. A bandage obtained by the process of claim 6.

9. A method for producing a cohesive, rigid or elastic bandage which adheres only to itself and not to the skin, hair and items of clothing, for fixing, compression and support dressings, and permanently elastic compression and support to dressings for medical purposes, comprising applying an adhesive substances in the form of fine particles in a quantity of 1,000 to 5,000 particles per 500 mm$^2$ in uniform distribution onto projecting fiber ends on both surfaces of a flat bandage, which consists of weft and warp, so that the adhesive adheres to the projecting fiber ends in a quantity of 10 to 40 g/m$^2$, by nozzle spraying in an eddy current field.

10. Cohesive, rigid or elastic bandage which only adheres to itself and not to skin, hair and clothing, for fixing dressings, compression dressings and support dressings and permanently elastic compression and support dressings for medical purposes, wherein the bandage has bonded to both sides a cohesive substance, said bandage consisting of a woven or knitted fabric and having fiber ends projecting from said fabric, said cohesive substance being fine particles of a size of 0.0000785 to 0.07 mm$^2$ of an adhesive, bonded to said fiber ends on both sides of the fabric in a uniform distribution of 1,000 to 5,000 particles per approximately 500 mm$^2$ in an application quantity in the order of magnitude of 10 to 40 g/m$^2$, wherein there is substantially no reduction in the porosity and elasticity of the fabric.

11. The bandage of claim 10 wherein the application quantity is from 15 to 20 g/m$^2$.

12. The bandage of claim 10 wherein the adhesive substance is rubber.

13. A method for producing a cohesive, rigid or elastic bandage which adheres only to itself and not to the skin, hair and items of clothing, for fixing, compression and support dressings, and permanently elastic compression and support to dressings for medical purposes, comprising applying an adhesive substances in the form of fine particles in a quantity of 1,000 to 5,000 particles per 500 mm$^2$ in uniform distribution onto projecting fiber ends on both surfaces of a flat bandage, which consists of warp of a woven or knitted fabric so that the adhesive adheres to the projecting fiber ends in a quantity of 10 to 40 g/m$^2$, by nozzle spraying in an eddy current field.

* * * * *